US012002557B2

(12) United States Patent
Thomas, III et al.

(10) Patent No.: US 12,002,557 B2
(45) Date of Patent: Jun. 4, 2024

(54) CREATING AND UPDATING PROBLEM LISTS FOR ELECTRONIC HEALTH RECORDS

(71) Applicants: Retrieve Medical, Inc., Basking Ridge, NJ (US); The Research Foundation for the State University of New York, Albany, NY (US)

(72) Inventors: Donald C. Thomas, III, St. Petersburg Beach, FL (US); Christopher E. Orlando, Verona, NJ (US)

(73) Assignees: RETRIEVE MEDICAL, INC., Basking Ridge (NI); THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 17/957,061

(22) Filed: Sep. 30, 2022

(65) Prior Publication Data

US 2024/0112767 A1   Apr. 4, 2024

(51) Int. Cl.
*G16H 10/60* (2018.01)
(52) U.S. Cl.
CPC ................... *G16H 10/60* (2018.01)
(58) Field of Classification Search
CPC .................................................. G06F 3/0641
See application file for complete search history.

(56) References Cited

U.S. PATENT DOCUMENTS

2010/0011282 A1*  1/2010  Dollard .................. G06F 40/169
                                              715/810
2016/0147949 A1*  5/2016  Bess .................... G06F 16/2365
                                              705/3

(Continued)

FOREIGN PATENT DOCUMENTS

WO    WO-2014134382 A1 *  9/2014   ............. G06F 16/93

OTHER PUBLICATIONS

Lee, D. H. K. (2014). The science and practice of SNOMED CT implementation (Order No. NS28408). Available from ProQuest Dissertations and Theses Professional. (1520453642). (Year: 2014).*

(Continued)

*Primary Examiner* — Christopher L Gilligan
*Assistant Examiner* — Emily Huynh
(74) *Attorney, Agent, or Firm* — Tutunjian & Bitetto, P.C.

(57) ABSTRACT

Systems and methods for maintaining an electronic health records system, including a server storing a medical records database. Requests for medical data for a patient in a master problem list are received from a user device, and appropriate list permissions are determined and granted for hierarchical derivative problem lists. Annotated data is received at the server from a user device based on annotations made to a derivative problem list, and problem lists are updated with the received annotated data in real time. The received annotated data is compared with current entries using natural language processing to detect duplicate entries, the duplicate entries are iteratively detected and removed from the master problem list, and non-duplicate entries are stored in autho- (Continued)

rized derivative problem lists based on the natural language processing and list update permissions for each of the derivative problem lists.

20 Claims, 9 Drawing Sheets

(56) References Cited

U.S. PATENT DOCUMENTS

| | | | |
|---|---|---|---|
| 2017/0140101 A1* | 5/2017 | Anderson | G16H 10/65 |
| 2017/0185718 A1* | 6/2017 | Naeymi-Rad | G16H 10/60 |
| 2018/0121605 A1* | 5/2018 | Allen | G16H 20/10 |
| 2021/0043286 A1 | 2/2021 | Ramakrishnan et al. | |
| 2022/0148691 A1* | 5/2022 | Katouzian | G16H 10/60 |

OTHER PUBLICATIONS

Wright, A., McCoy, A. B., Hickman, T. T. T., Hilaire, D. S., Borbolla, D., Bowes III, W. A., . . . & Sittig, D. F. (Oct. 1, 2015). Problem list completeness in electronic health records: a multi-site study and assessment of success factors. International journal of medical informatics, 84(10), 784-790.

* cited by examiner

CREATING AND UPDATING PROBLEM LISTS FOR ELECTRONIC HEALTH RECORDS

BACKGROUND

Technical Field

The present invention relates to automated creation and updating of problem lists for particular patients for Electronic Health Records (EHR) management, and more particularly to granting and/or restricting access to creating, viewing, and updating portions of problem lists for particular patients by a plurality of health care professionals with different specialties and problem list permissions in real time.

Description of the Related Art

Health Systems across the globe are focused on moving to Electronic Health Records (EHRs) both in the hospital and ambulatory settings to make patients' clinical information easily retrievable across settings. Improvements to the EHR that can streamline the ease of use and push valuable problem list information to the provider during the episode of care can both increase the quality of health care provided as well as enhance accurate reimbursement are needed and will find widespread application and adoption.

A "problem list" has been part of the documentation system used by physicians for many years. Traditionally, that method, known as the Weed system (e.g., A documentation system conventionally taught to all physicians), uses the SOAP format (Subjective, objective, assessment, plan) to structure clinical documentation. A central idea of the Weed system is that it keeps clinical notes organized and complete by indexing with the problem list. The problem list is a compendium of all problems that have been found for a particular patient in the patient's EHR. The list is generally kept in a named section of the patient's EHR and is intended to be exhaustive. The reason that the problem list has remained at the center of these patient considerations is that the index of problematic abnormalities found in a particular patient can vary on every visit, as annotated from the perspective of the clinician conducting the visit. However, conventionally, only problems pertinent to the patient visit get regular annotations, which can often result in incomplete patient records stored in an EHR system.

Traditionally, on an inpatient service, each patient has one designated physician (e.g., the Primary Managing Physician (PMP)) who has primary responsibility for effectively and efficiently driving that patient's care from admission to discharge. If the patient were attended by a single physician, then that clinician can easily separate, for example, active, chronic, and historical problems, and can write notes in SOAP format to address all pertinent problems. However, many other clinicians often are involved in the patient's care during a normal admission, they all make notations, which can include new problems, as seen through the perspective of their specialties.

In practice, many of these notations (e.g., new problems, observations, etc.) can be pertinent to both the specialty of the particular clinician and to long-term patient care, but may not be essential to address the medical problem of a particular patient which is driving the immediate clinical visit. Thus, as only problems pertinent to the immediate patient visit conventionally receive regular annotations, such important new problems are not updated to the EHR, which results in an incomplete EHR for the patient. Furthermore, real-time updating of Problem Lists (PLs) to a centralized server can result in reduced network speed during peak hours, and in some embodiments, the present invention can send less than all new information to a remote server for storage based on hierarchical list access and storage permissions of the present invention.

SUMMARY

An electronic health records (EHR) system including a server comprising a medical records database stored in a computer-readable storage medium operatively coupled to at least one processor device. The processor device receives requests for medical data for a patient in a master problem list (MPL) from one or more user devices, determines and grants one or more of the user devices appropriate list permissions for one or more of a plurality of hierarchical derivative problem lists (DPLs), and receives at the server annotated data related to the patient from one or more of the user devices based on annotations made to one or more of the DPLs. Problem lists (PLs) are updated in real time at the server with the received annotated data related from the one or more user devices. The updating includes comparing the received annotated data with current entries in the MPL using natural language processing (NLP) to identify duplicate entries, and iteratively detecting and removing the identified duplicate entries from the MPL and storing non-duplicate entries in appropriate authorized DPLs based on the NLP and hierarchical list update permissions for each of the DPLs.

A method for maintaining an electronic health records (EHR) system, including storing a medical records database in a computer-readable storage medium operatively coupled to at least one processor device, receiving requests for medical data for a patient in a master problem list (MPL) from one or more user devices, determining and granting one or more of the user devices appropriate list permissions for one or more of a plurality of hierarchical derivative problem lists (DPLs), receiving at the server annotated data related to the patient from one or more of the user devices based on annotations made to one or more of the DPLs, comparing the received annotated data with current entries in the MPL using natural language processing (NLP) identify duplicate entries, and iteratively detecting and removing the identified duplicate cranes from the MPL and storing non-duplicate entries in appropriate authorized DPLs based on the NLP and hierarchical list update permissions for each of the DPLs.

A non-transitory computer readable storage medium including a computer readable program operatively coupled to a processor device for maintaining an electronic health records (EHR) system, wherein the computer readable program when executed on a computer causes the computer to perform the steps of storing a medical records database in a computer-readable storage medium operatively coupled to at least one processor device, receiving requests for medical data for a patient in a master problem list (MPL) from one or more user devices, determining and granting one or more of the user devices appropriate list permissions for one or more of a plurality of hierarchical derivative problem lists (DPLs), receiving at the server annotated data related to the patient from one or more of the user devices based on annotations made to one or more of the DPLs, comparing the received annotated data with current entries in the MPL using natural language processing (NLP) to identify duplicate entries, and iteratively detecting and removing, the identified duplicate entries from the and storing non-duplicate entries in appropriate authorized DPLs based on the NLP and hierarchical list update permissions for each of the DPLs.

These and other features and advantages will become apparent from the following detailed description of illustrative embodiments thereof, which is to be read in connection with the accompanying drawings.

BRIEF DESCRIPTION OF THE DRAWINGS

The disclosure will provide details in the following description of preferred embodiments with reference to the following figures wherein.

DETAILED DESCRIPTION

Figure 1:
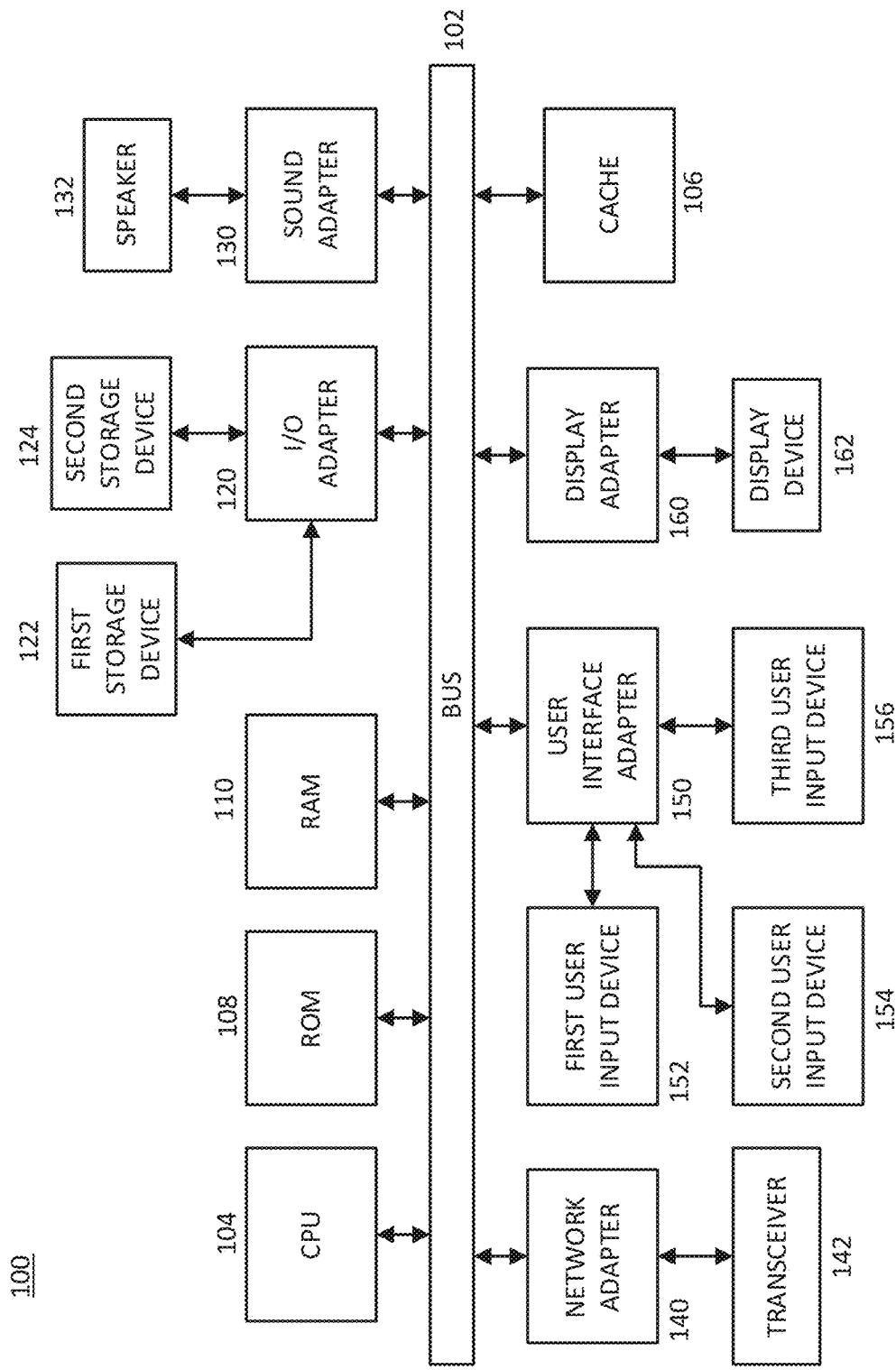
FIG. 1 shows an exemplary processing system to which the present principles may be applied, in accordance with embodiments of the present invention.

In accordance with the present invention, systems and methods are provided for automated creation and updating of problem lists for particular patients for Electronic Health Records (EHRs) management, and more particularly to granting and/or restricting access to creating, viewing, updating, and/or storing portions of problem lists for particular patients by a plurality of health care professionals with different specialties and problem list permissions in real time.

EHRs should improve identification and documentation of pertinent health issues. They should be faster and better than paper records. However, many Computerized Physician Order Entry (CPOE) and EHRs today result in physicians and nurses spending more time at the computer than at the bedside because data collection and entry, not patient care, becomes the focus, resulting in inefficiency and inaccuracy. With large amounts of data input to the EHR from multiple healthcare practitioners, there is the danger of data overload, resulting in the need to cull through extraneous information to find that which is pertinent, and the Problem List (PL) for particular patients can become cumbersome and include too much (or too little) information based on the updating. As these data entry tasks take time from the doctor-patient encounter, tasks such as updating a PL are often ignored, delayed until post-patient visit, include extraneous not-pertinent information, and/or left incomplete because of time constraints of physicians, nurses, etc., and/or lack of proper documentation and/or storage (e.g., permissions, location, etc.) for medical conditions (e.g., historical, or conditions causing current visit).

For example, existing methods for identifying historical medical data for a patient's PL in EHRs have relied primarily on costly and time-consuming manual chart review, and thus is incomplete and/or inaccurate for real-time (e.g., hospital) use. During a visit to the ER, voluminous amounts of information become available during the work-up, but because immediate treatment is being focused on the principal diagnosis some of the patient's other medical issues are often missed and/or not added to the patient's PL. As a result, accidental omissions from the patient's PL and/or EHR, and misdiagnosis can often occur in practice.

Moreover, in certain cases the physician may incorrectly decide to ignore particular medical conditions of a patient as an unimportant or a transient occurrence at least in part because of such inaccuracies. The physician may not take the time to list conditions that were present at the time of presentation and admission simply because of the amount of overwhelming data in the EHR and the inability to remember what important medical conditions are affecting this patient's current risk level, as such conditions are not in the patient's PL. Failure to document these medical conditions in the medical record (e.g., PL, EHR) leads to poor communication to the other providers in the care team and can lead to lack of coordination of patient care, increased lengths of stays, decreased revenue and unfortunately, poorer outcomes.

In various embodiments, the present invention can process historical and current documented clinical findings, using proven medical algorithms to indicate the presence of clinical conditions which appear to exist in the patient. These conditions can be identified according to definitions promulgated by CMS and/or authoritative professional society by specific names which convey relevance to clinicians, and which might impact upon the primary pathologic condition(s) which have caused the patient to present for evaluation. Conditions referred to here are actually factual items. (e.g., elevated chemical values like potassium or sodium levels, a positive physical diagnosis such as a pneumonia on x-ray or heart attack by EKG, etc.). The condition may be either a single factor or a cluster of factors, but they are factual, actual and not calculated. Rather they are collected as a compendium. The clinician can employ training, knowledge and judgment on each presented item to determine the relevance of the condition to the patient in real-time (e.g., during patient interaction), or at any time in accordance with various embodiments, and the patient's PL and/or EHR can be updated according to various aspects of the present invention.

While other Clinical Document Improvement (CDI) methods concentrate on analysis and correction of written clinical documentation as a retrospective basis of analysis (e.g., after a patient has been admitted to, treated, or discharged from a hospital), the present invention can utilize the raw data from clinical reporting systems to inform the clinician of previously defined conditions before final impressions are recorded for the clinical interaction, and further the PL and/or EHR can be updated in real-time, in accordance with various embodiments of the present invention.

A purpose of Clinical Document improvement systems (CDI) is to create the most accurate description of the patient possible. the difference is in the method employed to approach that result. The current state of the art is to post process or correct the observations that have been documented by the clinician after they have been recorded. The clinician's work can be reviewed, by either clinical documentation specialists, software, or some combination to determine whether there might be other factors that should be added to the original work to make it more precise. Then, queries (e.g., questions) are presented to the clinician who made the original notations which encourage review and possible revision of what has already been documented. This process is roughly analogous to spell or grammar checking a document after it has been written. There are several problems with this approach. It can be very time consuming for the clinician who still has to review the work already done, sometimes more than once. It also increases the risk that an outside reviewer will consider the activity as an attempt to "upcode" or artificially increase the severity of that patient's illness, retrospectively, to increase billings. In addition, it requires added rework for the physician which impinges on their work of the moment.

In some embodiments, data on the patient can be analyzed, sequentially testing its discovery definitions against each data item defined in its algorithms. The present invention can utilize Natural Language Processing (NLP) to extract relevant target data from text, speech, etc. (e.g., medical professional input during patient visit), or any sort of structured or unstructured data records to, for example, process, categorize, sort, and/or update a patient's PL and/or EHR with the unstructured data, which can be transformed into keywords or encoded strings for categorizing, sorting, and accessing the data, in accordance with various embodiments. When a targeted diagnosis or data point is found, it can be collected, pre-defined clusters of data and diagnoses can be assembled, according to rules, and held for display.

In some embodiment, hierarchical sorting and categorizing of data and/or PLs can assign access levels to documentation and certain actions which may be formally defined, but not consistently regulated. In practice, PLs are cumbersome and include, for example, wholly disorganized natural language notes from many medical professionals in which some entries are duplicates, some are not appropriate, some have been entered by staff without the proper credentials, etc. Thus, there is a need for consistent automated administration of clinical privileges to be defined to fit current practices into navigable rules, as the number of daily interactions with patients by a plurality of medical professionals and the large amount of data entered into one or more PLs during treatment is often entered incorrectly or does not comply with hospital and/or governmental regulations for record keeping.

A goal of the present invention is to enable updating in real-time of PLs while minimizing network resource requirements for such updating, as will be described in further detail herein below. The present invention can minimize such network resource requirements and automatically navigate and regulate complex clinical relationships and responsibilities which dictate which medical professional is responsible for patients at particular stages in treatment when there are being cared for by multiple clinicians simultaneously, in accordance with aspects of the present invention.

In various embodiments, the present invention can enable the emergency room physician to run the program inside the electronic medical record prior to the patient's admission and pulls together any vital signs, labs or radiology values from the patient's current encounter or in some instances, past encounters. Significant criteria found by the software are pushed to the PL of the ER physician (or other medical professionals depending on access to particular PLs) for access and/or updating during the patient's medical visit.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects. Furthermore, embodiments of the present invention may take the form of a computer program product embodied in one or more computer readable medium(s) having computer readable program code embodied thereon.

Any combination of one or more computer readable medium(s) may be employed. The computer readable medium may be a computer readable signal medium or a computer readable storage medium. A computer readable storage medium may be, but is not limited to, an electronic, magnetic, optical, electromagnetic, infrared, or semiconductor system, apparatus, or device, or any combination thereof. Other examples of the computer readable storage medium may include, but are not limited to, an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any combination thereof. In this document, a computer readable storage medium may be any tangible medium that can contain, or store a program for use by or in connection with a computing system, apparatus, or device.

Program code embodied on a computer readable medium may be transmitted using any suitable medium, including but not limited to wireless, wireline, optical fiber cable, etc., or any combination thereof. Computer program code for carrying out operations for aspects of the present invention may be written in any combination of one or more programming languages, including, but not limited to any general-purpose programing language (e.g., PHP, Java, C++, etc.) and/or domain-specific programing language (e.g., HTML, SQL, etc.). The program code may execute fully on the user's computer/mobile device, partially on the user's computer/mobile device, as stand-alone software, partially on the user's computer/mobile device and partially on a remote computer/mobile device, or entirely on a remote computer or server. The remote computer may be connected to the user's computer through any type of network (e.g., a local area network (LAN), wide area network (WAN), a connection to an external computer (e.g., over the Internet using an Internet Service Provider), etc.).

Aspects of the present invention are described below with reference to flowchart illustrations and/or block diagrams of methods, systems and computer program products according to embodiments of the present invention. It is noted that each block of the flowcharts and/or block diagrams, and combinations of blocks in the flowcharts and/or block diagrams, may be implemented by computer program instructions.

These computer program instructions may be sent to a processor of any type of computing system (e.g., general purpose computer, special purpose computer, or other programmable data processing apparatus to produce a machine), such that the instructions, which execute by the processor of the computing system, create a means for implementing the functions/instructions/acts specified in the flowcharts and/or block diagram block or blocks. These computer program instructions may also be stored in a computer readable medium that can instruct any computing device to function in a particular manner, such that the instructions stored in the computer readable medium produce an article of manufacture including instructions which implement the function/instruction/act specified in the flowchart and/or block diagram block or blocks.

The computer program instructions may also be loaded onto a computer, mobile device, other programmable data processing apparatus, or other devices to cause a series of operational steps to be performed on any computing system to produce a computer implemented process such that the instructions which execute on the computer or other programmable apparatus provide processes for implementing the functions/acts specified in the flowcharts and/or block diagram block or blocks.

A computer readable signal medium may include a propagated data signal with computer readable program code embodied therein (e.g., baseband, part of a carrier wave, etc.). Such a propagated signal may take any of a variety of forms, including, but not limited to, electro-magnetic, optical, or any combination thereof. A computer readable signal medium may be any computer readable medium that is not a computer readable storage medium and that can communicate, propagate, or transport a program for use by or in connection with a computing system, apparatus, or device.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The flowchart and block diagrams in the figures illustrate the architecture, functionality, and operation of possible implementations of systems, methods and computer program products according to various embodiments of the present invention. Each block in the flowchart or block diagrams may represent a module, segment, or portion of code, which comprises one or more executable instructions for implementing the specified logical function(s), and in some alternative implementations of the present invention, the functions noted in the block may occur out of the order noted in the figures. For example, two blocks shown in succession may, in fact, be executed substantially concurrently, may sometimes be executed in reverse order, or may be executed in any other order, depending on the functionality of a particular embodiment.

It is also noted that each block of the block diagrams and/or flowchart illustration, and combinations of blocks in the block diagrams and/or flowchart illustration, can be implemented by specific purpose hardware systems that perform the specific functions/acts, or combinations of special purpose hardware and computer instructions according to the present principles.

Referring now to the drawings in which like numerals represent the same or similar elements and initially to FIG. 1, an exemplary processing system 100, to which the present principles may be applied, is illustratively depicted in accordance with embodiments of the present principles. The processing system 100 includes at least one processor (CPU) 104 operatively coupled to other components via a system bus 102. A cache 106, a Read Only Memory (ROM) 108, a Random Access Memory (RAM) 110, an input/output (I/O) adapter 120, a sound adapter 130, a network adapter 140, a user interface adapter 150, and a display adapter 160, are operatively coupled to the system bus 102.

A first storage device 122 and a second storage device 124 are operatively coupled to system bus 102 by the I/O adapter 120. The storage devices 122 and 124 can be any of a disk storage device (e.g., a magnetic or optical disk storage device), a solid-state magnetic device, and so forth. The storage devices 122 and 124 can be the same type of storage device or different types of storage devices.

A speaker 132 is operatively coupled to system bus 102 by the sound adapter 130. A transceiver 142 is operatively coupled to system bus 102 by network adapter 140. A display device 162 is operatively coupled to system bus 102 by display adapter 160.

A first user input device 152, a second user input device 154, and a third user input device 156 are operatively coupled to system bus 102 by user interface adapter 150. The user input devices 152, 154, and 156 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present principles. The user input devices 152, 154, and 156 can be the same type of user input device or different types of user input devices. The user input devices 152, 154, and 156 are used to input and output information to and from system 100.

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 100 are readily contemplated by one of ordinary skill in the art given the teachings of the present principles provided herein.

Moreover, it is to be appreciated that systems 400, 500, 600, and 700, described below with respect to FIGS. 4, 5, 6, and 7, respectively, are systems for implementing respective embodiments of the present invention. Part or all of processing system 100 may be implemented in one or more of the elements of systems 400, 500, 600, and 700.

Figure 2:
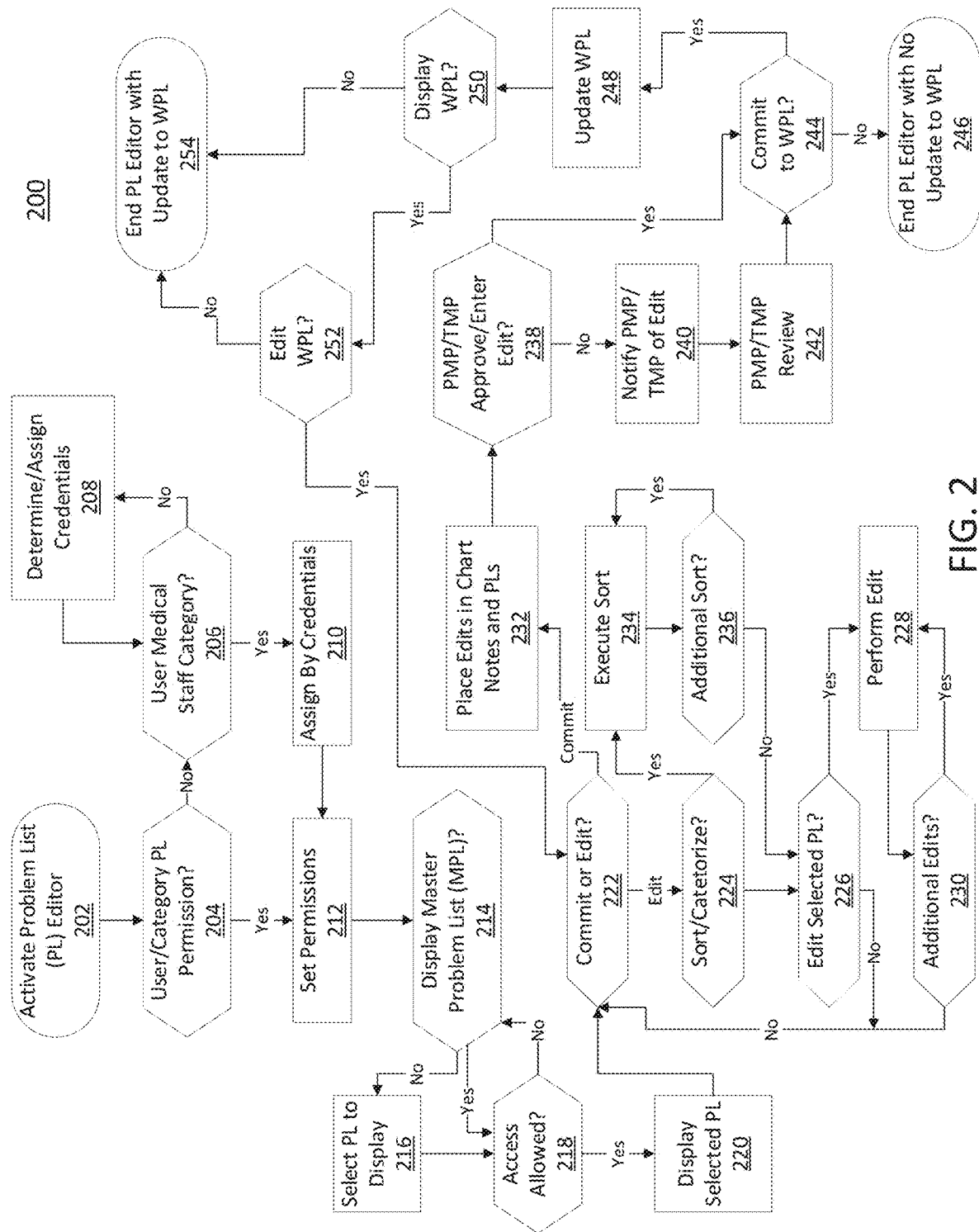
FIG. 2 is a block/flow diagram showing a method for creating, updating, and/or controlling access to problem lists for Electronic Health Records, in accordance with embodiments of the present invention.
Figure 3:
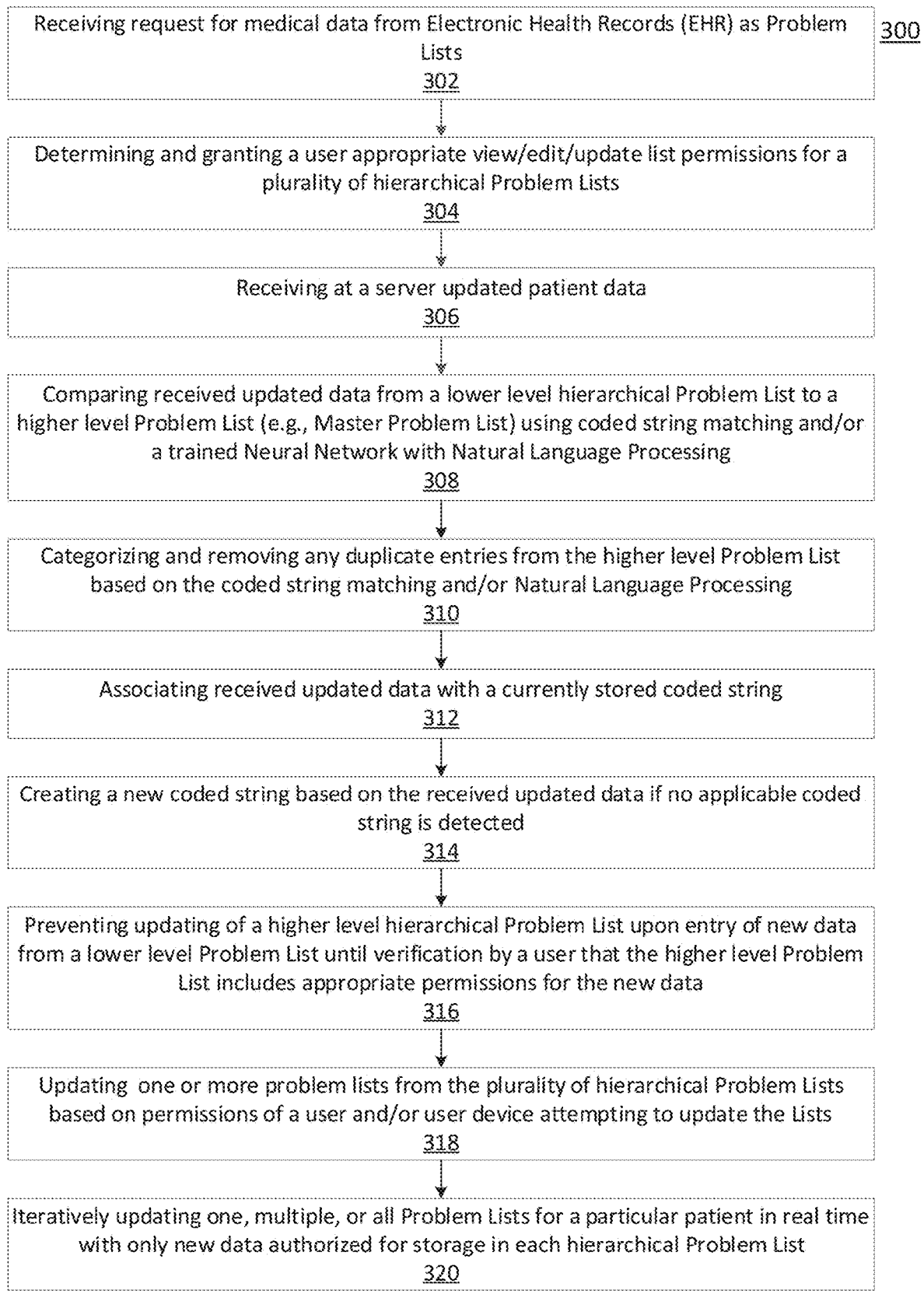
FIG. 3 is a diagram showing a method for creating, updating, and/or controlling access to problem lists for Electronic Health Records, in accordance with embodiments of the present invention.
Figure 8:
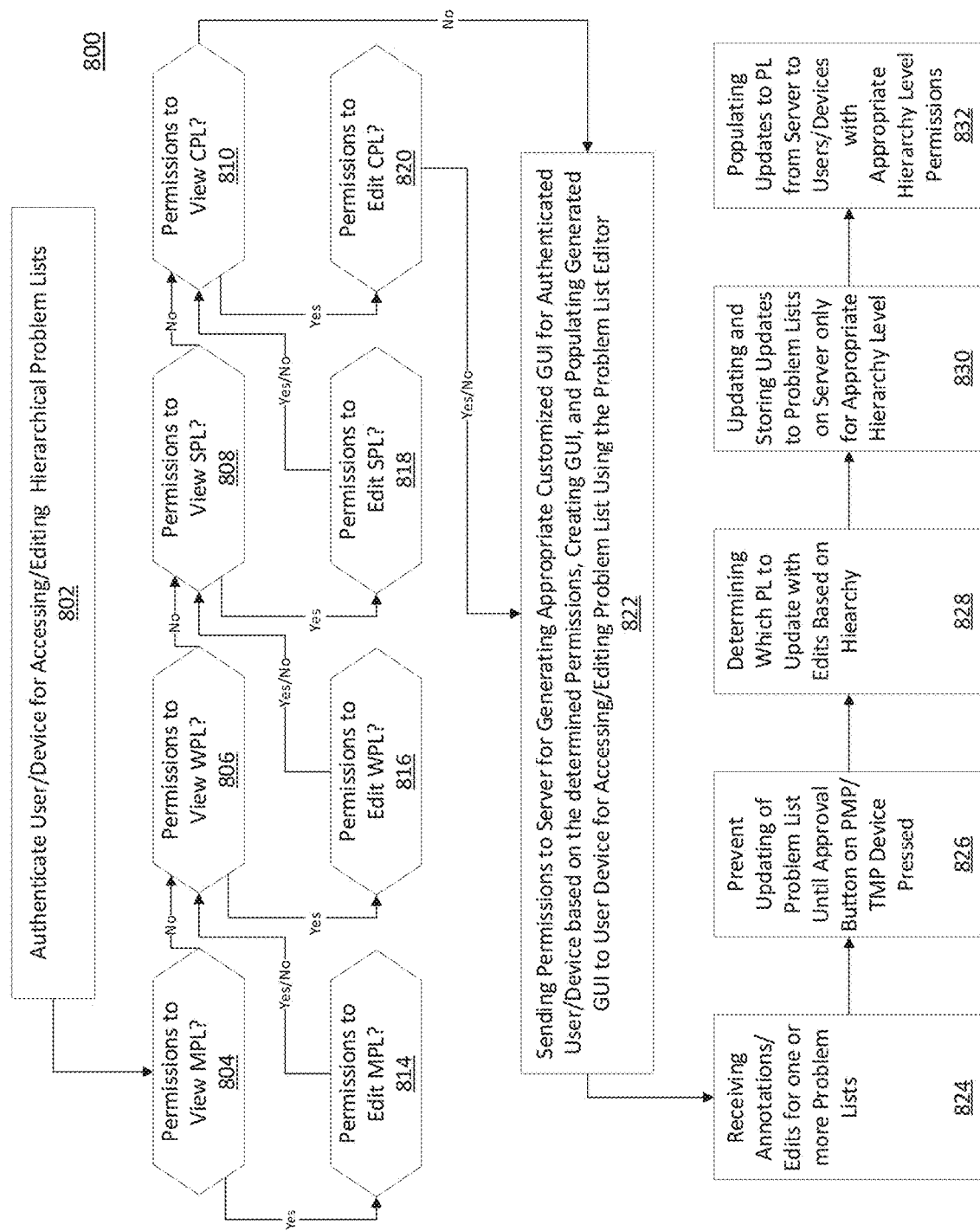
FIG. 8 is a diagram showing a method for authenticating and applying appropriate access and storage permissions for users and/or devices for creating, updating, and/or controlling access to problem lists for Electronic Health Records, in accordance with embodiments of the present invention.

Further, it is to be appreciated that processing system 100 may perform at least part of the method described herein including, for example, at least part of methods 200, 300, and 800 of FIGS. 2, 3, and 8, respectively. Similarly, part or all of systems 400, 500, 600, and 700 may be used to perform at least part of methods 200, 300, and 800 of FIGS. 2, 3, and 8, respectively.

Referring now to FIG. 2, a block/flow diagram showing a method 200 for creating, updating, and/or controlling access to problem lists (PLs) for Electronic Health Records (EHRs) is illustratively depicted in accordance with embodiments of the present principles.

Generically, a PL is the tool which can function as a compass which ensures that a patient's care remains on course throughout a single, or multiple medical visits. In practice, different versions of PLs are utilized depending on whether the patient is an inpatient or an outpatient.

Healthcare students, professionals, etc. are taught to list all abnormalities (both acutely discovered and already known) and formulate management plans for each for particular patients. Depending on the clinical scenario, the list may be narrowed by a medical professional. Specialists may focus on issues impacting their areas of interest while general practitioners usually have a wider view. Each problem can then be followed to its resolution or until the problem has been at least stabilized. This simple formulation can become problematic when multiple individuals (e.g., multiple healthcare professionals working on a patient during one or multiple visits to one or more medical facilities for treatment) are involved. As the number of perspectives multiply, the list quickly becomes unwieldly and difficult to use in real time in practice. As more types of healthcare workers access the list, the more diverse the entries become, and such entries are all added into a master problem list, which must be sifted through by medical professionals to locate relevant information for the patient/patient visit.

Although this diversity may offer a "more complete" depiction of the patient, it also makes it harder for the primary clinician to follow the "central" issues relevant to the patient's medical visit (e.g., outpatient, hospitalization, referral, etc.). Problem list reconciliation is also made more difficult under the "too many cooks" principle, as many health professionals generally work on a patient during a medical visit, and each can notate the master problem list with unsorted data entered as natural language, and processed prior to categorizing and/or uploading the data into one or more problem lists stored locally or on a remote server (e.g., cloud based).

PLs has been part of the documentation system used by physicians and other healthcare professions for many years. Traditionally, that method, known as the Weed system (e.g., a documentation system taught to physicians), uses the SOAP format (i.e., Subjective, objective, assessment, plan) to structure clinical documentation. The central idea of the Weed system is that it keeps clinical notes organized and somewhat complete by indexing with the PL for a patient. The PL is a compendium of all problems that have been found on a particular patient. This PL is kept in a named section of the patient's record and is intended to be exhaustive, but often is incomplete in practice. The reason that the problem list has remained at the center of these patient considerations is that the index of problematic abnormalities found in a particular patient can vary on every visit, as annotated from the perspective of the clinician or other healthcare professional conducting the visit with the patient. In practice, only problems pertinent to the patient visit get regular annotations to the PL and/or EHR of a patient.

This system, however, includes drawbacks which prevent accurate and complete documentation in a PL or EHR of a patient at least in part because everyone that has clinical contact (e.g., Emergency Room Nurse, general practitioner, specialist, etc.) with the patient finds problems germane to their specialty's perspective and wants those problems added to the problem list, but not all problems are appropriate to be placed in the PL.

Traditionally, on an inpatient service, each patient has one designated physician (e.g., a Primary Managing Physician (PMP)) who has primary responsibility for effectively and efficiently driving that patient's care from admission to discharge. If the patient were attended by a single physician, there would not as much difficulty in maintaining and updating a PL for a patient, as that clinician would separate active, chronic, and historical problems, and writing notes in SOAP format to address all pertinent problems, which can all then be updated in the PL and/or EHR for a patient.

However, in practice, many other clinicians (e.g., nurse, Temporary Managing Physician (TMP), Clinical Consultant Personnel (CCP), physicians assistants, respiratory therapists, Occupational therapist, speech therapists, social workers, etc.) may get involved in the patient's care during a normal admission, and they generally all make notations which can include new problems, as seen through the perspective of their specialties. Some of those problems are very pertinent to both their specialty and to long term patient care but may not be essential for the patient problems which are driving the immediate clinical episode. Numerous attempts have been made to correct problems with the PL management but have failed, short of restricting edit access to the list itself to anyone except the PMP, no solution has been achieved for accurate and efficient management of PLs, in particular when a patient is seen by multiple healthcare professionals during a visit or visits to a medical facility.

As such, some of the notations may not be appropriate to include in the Master Problem List (MPL), or other derivative PLs (e.g., Working Problem List (WPL), Specialty Problem List (SPL), Custom Problem List (CPL), etc.). It is noted that although only MPL, WPL, SPL, and CPL PLs are discussed above, any sort of PL can be created for particular types of practitioners (e.g., physician, nurse, etc.), departments (e.g., cardiology, emergency, etc.), and/or specialized devices (e.g., including building/room proximity sensors), in accordance with various embodiments of the present invention. Similarly, although only a nurse, PMP, TMP, and CCP are discussed above, any sort of designation for different healthcare professionals can be utilized, and a customized PL can be constructed for these different healthcare professionals, in accordance with various embodiments of the present invention.

The present invention can manage a PL for a patient by enabling only appropriate individuals to be able to view the Master Problem List (MPL), and to interact with their Specialty Problem List (SPL) allowing them to edit, sort and view problems relevant to them without altering or restricting the use of any other PLs by others. Additionally, the patient's Primary Managing Physician (PMP) can utilize and control a Working Problem List (WPL) which will drive most documentation issues on any current admission. This WPL can be restricted from viewing and/or editing to particular types of healthcare professionals (e.g., PMP, TMP, CCP, nurse, etc.) or specific individual healthcare professionals (e.g., Doctor X, Nurse Y, etc.), or access can be expanded to include additional groups upon such a designation by the PMP, in accordance with aspects of the present invention.

The present invention utilizes a novel system and method for PL management, which protects the traditional uses of the PL and creates new functionalities for accessing, updating, and/or storing data in a PL and/or EHR for a patient. It is noted that a PMP is a physician who is responsible for the active daily care of a patient including admission and discharge documentation. A TMP is a physician who receives a transfer of control of patient care (e.g., for call coverage of specific procedures (e.g., surgery)), and a TMP once designated as receiving control will inherit some or all abilities from the PMP with respect to the PL (e.g., night staff taking control of approval and other functions for the MPL or other PLs until the PMP returns and can retake control, patient transferred to CCMD with a SPL for the patient and PMP can transfer PMP status to the CCMD for the duration of visit to specialty unit, etc.). A CCP is a clinician with access to a patient's chart resulting from requests to perform a specialized function (e.g., Rehab after surgery, speech therapy and assistance with activities of regular life after stroke, exercise after heart attack, etc.) for the patient.

In accordance with embodiments of the present invention, a plurality of hierarchical PLs can be utilized to improve usability and accuracy of the PLs and EHR for a patient. The MPL is a master list of all problems annotated in an EHR of a patient, and this list can be automatically updated whenever any of the derivative problem lists (e.g., WPL, SPL, CPL, etc.) have been altered. In some embodiments, interaction and/or approval to update by a user (e.g., PMP) may be required prior to pushing any updates from the derivative problem lists into the MPL and/or EHR, in accordance with aspects of the present invention. The WPL can be controlled by the PMP, and can function as an index of the patient's active governing PL. This WPL can be utilized to guide the patient's therapeutic course throughout a patient visit to a medical facility for treatment. The SPL is a PL generated by and specific to a subgroup within a medical facility/institution (e.g., cardiology, emergency medicine, neurology, etc.). The CPL is a PL generated by and specific to a particular clinician (e.g., nurse, emergency room physician, etc.).

In an embodiment, a PL editor can be activated in block 202, and PL permissions for a user, category, device, etc. are determined in block 204. If permissions are not granted for a particular user, category, device, etc., a user medical staff category can be determined for the user in block 206, and credentials may be determined and assigned for the user, category, device, etc. in block 208 in accordance with aspects of the present invention. Once a medical staff category is determined to be present in block 206, the user, category, device, etc. can be assigned to an appropriate problem list in block 210, and permissions may be set in block 212. If the user, category, device, etc. has been determined to include the appropriate PL permissions in block 204, permissions can be set for particular PLs in block 212, in accordance with aspects of the present invention.

In an embodiment, in block 214, system can prompt a user to determine whether the user wants to display an MPL. If the user selects no in block 214, then a user can select a different PL list to display in block 216. If access is determined to be allowed for that user in block 218, then the selected PL can be displayed in block 220 on a device of a user. If no access is allowed, the system reverts to block 214 and can iterate until a PL with access permissions for the user is identified in block 218. Upon viewing the PL, a user with approval authority (e.g., PMP, TMP, CCP, nurse, critical care medicine department (CCMD), etc.) can either commit (e.g., with no edits) the PL to charts and/or another PL, and if no edits have been made to the PL, the PL Editor can end with no update to the WPL in block 246, in accordance with embodiments of the present invention. It is to be appreciated that in some embodiments, all PLs can be viewed and/or edited by all authenticated users, while in other embodiments, viewing and/or editing of some PLs can be restricted based on determined PL permissions for each of a plurality of end users, in accordance with aspects of the present invention.

An exemplary access/edit chart for different groups can be found hereinbelow:

TABLE 1

| Group | MPL | | WPL | | SPL | | CPL | |
| --- | --- | --- | --- | --- | --- | --- | --- | --- |
| | VIEW | EDIT | VIEW | EDIT | VIEW | EDIT | VIEW | EDIT |
| PMP | X | X | X | X | X | X | X | X |
| TMP | X | X | X | X | X | X | X | X |
| CCMD | X | | X | | X | X | X | X |
| CCP | X | | X | | X | | X | X |

In an embodiment, upon viewing the PL, if a user (e.g., PMP, TMP, CCP, nurse, etc.) has edited the viewed PL in block 222, the free-form edits can be sorted and/or categorized by executing Natural Language Processing by training a neural network to, for example, determine categories for sorting based on the free form edits and already present categories for particular medical events/diseases in the PL and/or EHR. If the edits do not appropriately fit into any of the already present categories, the NLP engine can be utilized to create a new appropriate category, which can be added to the PL and/or EHR automatically, or can be prevented from being created until a particular user (e.g., PMP) receives an alert (e.g., pop up window, alarm sound, etc.) and approves the creation of the new PL category, in accordance with aspect of the present invention.

In some embodiments, if sorting/categorizing (e.g., sorting/categorizing data from/into one or more PLs) is selected in block 224, then sorting can be executed in block 234 and the results can be presented to the user to determine if additional sorting/categorizing is desired to perform again. If additional sorting/categorizing is selected in block 236, then the sorting/categorizing can be iterated in block 234 until additional sorting/categorizing is not selected in block 236. In block 226, if a user selects to edit the selected PL, then the editing of the PL can be executed in block 228 and the results can be presented to the user to determine if additional editing is desired to be performed. If additional editing is selected in block 230, then the editing can be iterated in block 228 until additional editing is not selected in block 230, and the user can select whether to commit the edits and place the edits in chart notes and the selected PL in block 232 or whether to perform additional sorting and/or edits in blocks 224, 226, 228, 230, 234, and 236, in accordance with aspects of the present invention.

In an embodiment, once the edits are placed in chart notes and or the selected PL in block 232, it is determined whether the edits have been approved by an appropriate staff member (e.g., with approval authority granted) responsible for the patient (e.g., PMP, TMP, etc.) in block 238. It is noted that any staff member can be designated as an appropriate staff member for such approval, but for the sake of brevity, an appropriate staff member will be referred to as an PMP/TMP for the sake of illustration hereinbelow. If the edits are determined to have been approved by the PMP/TMP, then the PMP determines whether the edits should be committed and updated to the WPL in block 244. If the edits have not been approved by the PMP/TMP, then an alert (e.g., popup, audible alarm, etc.) can be sent to a device of the PMP/TMP to notify the PMP/TMP of the pending edit. The PMP/TMP can then review the updates in block 242 to determine whether the edits should be committed and updated to the WPL in block 244.

In an embodiment, if the PMP/TMP selects to not commit the updates to the WPL in block 244, then the PL editor can end with no updates to the WPL in block 246. If the PMP/TMP selects to commit the updates to the WPL, then the WPL can be updated accordingly in block 248. In block 250, if the PMP/TMP makes a selection to display the updated WPL, the PMP/TMP can select whether to make further edits to the WPL in block 252. If the PMP/TMP selects editing the WPL in block 252, then the process can be iteratively repeated beginning at block 222, in accordance with aspects of the present invention. If the PMP selects to not display the WPL in block 250 or selects to not edit the WPL in block 252, then the PL editor can end in block 254 with the updates to the WPL stored on a local device (e.g., for later updating to a server) and/or remote computing device (e.g., cloud, remote server, etc.) in real time so that other medical professionals attending to the patient can access the updates immediately (e.g., within seconds or minutes), which is particularly important when more than one medical professional is working on a patient to ensure proper and timely care during a medical visit.

As an illustrative example, using different PLs for a patient receiving care at a hospital, it can be assumed that a patient with congestive heart failure is admitted to a hospital with a severe exacerbation which has resulted in decompensation. The patient is admitted because of the hypoxia. During the work up (e.g., medical visit) it is found that the patient has a positive EKG, positive chest x-ray, anemia, renal insufficiency, obesity, peripheral edema, and osteopenia. All of these issues can be entered into the problem list, and consultants can be called in to assist, and they generally produce derivative problems:

In an embodiment, an exemplary Master Problem List (MPL) can include the following:
  1. Hypoxia (ER)
  2. Positive EKG (ER)
  3. Pleural Effusion (ER)
  4. Peripheral Edema (ER)
  5. Right lower lobe infiltrate (ER)
  6. Anemia (ER)
  7. Renal insufficiency (Hospitalist)
  8. RLL Pneumonia (Hospitalist)
  9. Complex anemia due to iron deficiency and B12 deficiency (Hematology)
  10. Acute on Chronic Renal Insufficiency (Nephrology)
  11. Congestive Heart Failure (cardiology)
  12. Paroxysmal Atrial Fibrillation
  13. Old inferior wall myocardial infarction (Cardiology)
  14. BMI 35 (cardiology)
  15. Osteopenia (Radiology)

In an embodiment, the MPL can be generated automatically, based on the entries into the EHR by the various health care professionals (e.g., clinicians, nurses, consultants, etc.). All of the clinicians can see and work off of the MPL, but this growing list has problems that do not need to be completed before patient discharge for the present visit, and as such, are extraneous and cause reduced usability of the system at least due to the vast amount of data included which is not relevant to the present visit of the patient. Indeed, many of the problems on the MPL do not need to be resolved (or cannot be resolved) during the present visit, and thus, can be removed to improve the usability, accuracy, and relevance of information when creating derivative lists (e.g., WPL, SPL, CPL, etc.), in accordance with aspects of the present invention.

In an embodiment, a PMP can construct a Working Problem List (WPL) for a particular patient based off the MPL, and an exemplary WPL related to the above MPL can include the following:
  1. Hypoxia (ER)
  2. Renal insufficiency (Hospitalist)
  3. RLL Pneumonia (Hospitalist)
  4. Complex anemia due to iron deficiency and B12 deficiency (Hematology)
  5. Acute on Chronic Renal Insufficiency (Nephrology)
  6. Congestive Heart Failure (cardiology)
  7. Paroxysmal Atrial Fibrillation (Cardiology)
  8. Old inferior wall myocardial infarction (Cardiology)

In an embodiment, each of a plurality of specialists (e.g., cardiologist, urologist, surgeon, etc.) can have customized Specialty Problem Lists (SPLs) for their particular specialty. An exemplary SPL for cardiology can include the following:
  1. Congestive Heart Failure (cardiology)
  2. BMI 35 (cardiology)
  3. Paroxysmal Atrial Fibrillation (Cardiology)
  4. Old inferior wall myocardial infarction (Cardiology)

In an embodiment, specific specialists (e.g., a particular cardiologist, urologist, surgeon, etc.) can utilize a Custom Problem List (CPL) to include not only items from the SPL for their specific specialty, but also to add other items that the specific specialist determines should be added as important for the particular patient's care. An exemplary CPL for a specific cardiologist can include the following:
  1. Congestive Heart Failure (cardiology)
  2. BMI 35 (cardiology)
  3. Paroxysmal Atrial Fibrillation (Cardiology)
  4. Old inferior wall myocardial infarction (Cardiology)
  5. Hypoxia (ER)
  6. Complex anemia due to iron deficiency and B12 deficiency (Hematology)

It is to be appreciated that the above-presented lists are exemplary, and can include any amount or any sort of data relevant to a particular patient, in accordance with various aspects of the present invention.

Referring now to FIG. 3, a diagram showing a method 300 for creating, updating, and/or controlling access to problem lists for Electronic Health Records is illustratively depicted in accordance with embodiments of the present invention.

In an embodiment, in block 302, a request for medical data from one or more Electronic Health Records (EHRs) as problem lists can be received at a server (e.g., local or remote server). In block 304, it can be determined whether the user requesting the medical data has view, edit, and/or update list permissions for one or more of a plurality of hierarchical PLs, and the user can be provided with appropriate access after authentication. In block 306, updated patient data can be received at a server (e.g., local or remote) for a particular patient. In block 308, the received updated data from a lower-level hierarchical PL can be compared with data from a higher-level PL (e.g., MPL) using coded string matching (e.g., hash function, keyword, etc.) and/or by training a Natural Language Processing (NLP) engine using a neural network to identify, categorize, and/or sort free form data entered by users, in accordance with aspects of the present invention.

In an embodiment, in block 310, input data can be categorized (e.g., using NLP, hash functions, keywords, etc.) and any duplicate entries can be removed from a higher-level PL (e.g., MPL) based on the coded string matching and/or the natural language processing. In block 312, received updated data can be associated with a currently stored coded string, and if no applicable coded string can be detected (e.g., using NLP, coded string matching, etc.), then a new coded string can be created based on the received updated data in block 314. In block 316, updating of a higher-level hierarchical PL can be prevented upon entry of new data from a lower level PL until verification by an appropriate user (e.g., user with approval authority granted) that the higher-level PL includes appropriate permissions and/or categories for the new data, in accordance with aspects of the present invention.

In block 318, one of more PLs from the plurality of hierarchical PLs can be updated based on the permissions of a user and/or user device attempting to update the PLs. In block 320, all PLs for which updates have been approved can be automatically and iteratively updated for particular patients with only new data authorized for storage in each hierarchical PL, in accordance with aspects of the present invention. In accordance with various embodiments, such iterative updating of PLs in real time ensures that medical professionals assisting patients have all the updated and necessary information to care for a patient essentially immediately (e.g., seconds or minutes), and further reduces network requirements for updating the PLs by sending small amounts of data rather than uploading all new data to PLs at a particular time of day, as is conventionally performed post-shift by medical professionals.

Figure 4:
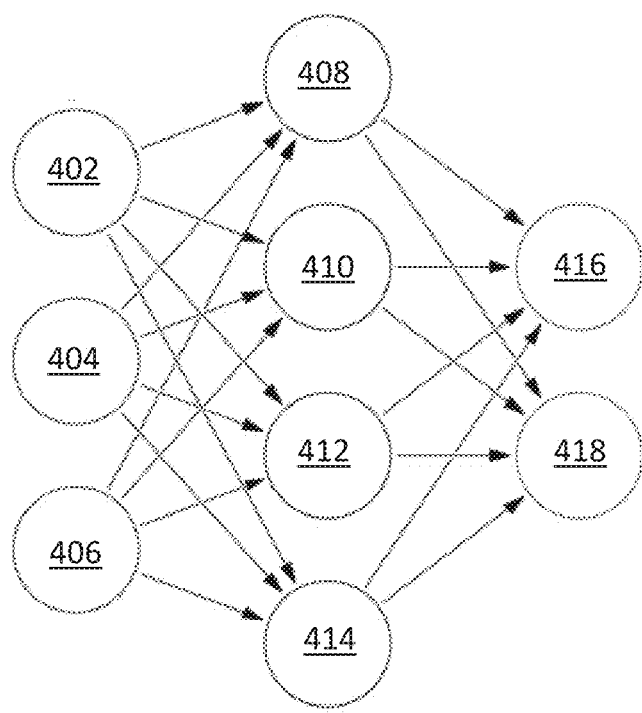
FIG. 4 is a generalized diagram showing an exemplary neural network for use in creating, updating, and/or controlling access to problem lists for Electronic Health Records, in accordance with embodiments of the present invention.

Referring now to FIG. 4, a generalized diagram 400 showing an exemplary neural network for use in creating, updating, and/or controlling access to problem lists for Electronic Health Records is illustratively depicted in accordance with embodiments of the present invention.

An artificial neural network (ANN) is an information processing system that is inspired by biological nervous systems, such as the brain. One element of ANNs is the structure of the information processing system, which includes a large number of highly interconnected processing elements (called "neurons") working in parallel to solve specific problems. ANNs are furthermore trained using a set of training data, with learning that involves adjustments to weights that exist between the neurons. An ANN is configured for a specific application, such as pattern recognition or data classification, through such a learning process.

Although a specific structure of an ANN is shown, having three layers and a set number of fully connected neurons, it should be understood that this is intended solely for the purpose of illustration. In practice, the present embodiments may take any appropriate form, including any number of layers and any pattern or patterns of connections therebetween.

ANNs demonstrate an ability to derive meaning from complicated or imprecise data and can be used to extract patterns and detect trends that are too complex to be detected by humans or other computer-based systems. The structure of a neural network is known generally to have input neurons 102 that provide information to one or more "hidden" neurons 104. Connections 108 between the input neurons 102 and hidden neurons 104 are weighted, and these weighted inputs are then processed by the hidden neurons 104 according to some function in the hidden neurons 104. There can be any number of layers of hidden neurons 104, and as well as neurons that perform different functions. There exist different neural network structures as well, such as a convolutional neural network, a maxout network, etc., which may vary according to the structure and function of the hidden layers, as well as the pattern of weights between the layers. The individual layers may perform particular functions, and may include convolutional layers, pooling layers, fully connected layers, softmax layers, or any other appropriate type of neural network layer. Finally, a set of output neurons 106 accepts and processes weighted input from the last set of hidden neurons 104.

This represents a "feed-forward" computation, where information propagates from input neurons 102 to the output neurons 106. Upon completion of a feed-forward computation, the output is compared to a desired output available from training data. The error relative to the training data is then processed in "backpropagation" computation, where the hidden neurons 104 and input neurons 102 receive information regarding the error propagating backward from the output neurons 106. Once the backward error propagation has been completed, weight updates are performed, with the weighted connections 108 being updated to account for the received error. It should be noted that the three modes of operation, feed forward, back propagation, and weight update, do not overlap with one another. This represents just one variety of ANN computation, and that any appropriate form of computation may be used instead.

To train the ANN, training data can be divided into a training set and a testing set. The training data includes pairs of an input and a known output. During training, the inputs of the training set are fed into the ANN using feed-forward propagation. After each input, the output of the ANN is compared to the respective known output. Discrepancies between the output of the ANN and the known output that is associated with that particular input are used to generate an error value, which may be backpropagated through the ANN, after which the weight values of the ANN may be updated. This process continues until the pairs in the training set are exhausted.

In an embodiment of the present invention, an ANN can be utilized to train a Natural Language Processing (NLP) engine to iteratively identify and categorize free form data entered into a PL (as described in further detail with regard to FIG. 2) for sorting and/or categorizing of data entered by one of more users (e.g., medical professionals) into one or more PLs, in accordance with aspects of the present invention.

After the training has been completed, the ANN may be tested against the testing set, to ensure that the training has not resulted in overfitting. If the ANN can generalize to new inputs, beyond those which it was already trained on, then it is ready for use. If the ANN does not accurately reproduce the known outputs of the testing set, then additional training data may be needed, or hyperparameters of the ANN may need to be adjusted.

ANNs may be implemented in software, hardware, or a combination of the two. For example, each weight 108 may be characterized as a weight value that is stored in a computer memory, and the activation function of each neuron may be implemented by a computer processor. The weight value may store any appropriate data value, such as a real number, a binary value, or a value selected from a fixed number of possibilities, that is multiplied against the relevant neuron outputs. Alternatively, the weights 108 may be implemented as resistive processing units (RPUs), generating a predictable current output when an input voltage is applied in accordance with a settable resistance, in accordance with aspects of the present invention.

Figure 5:
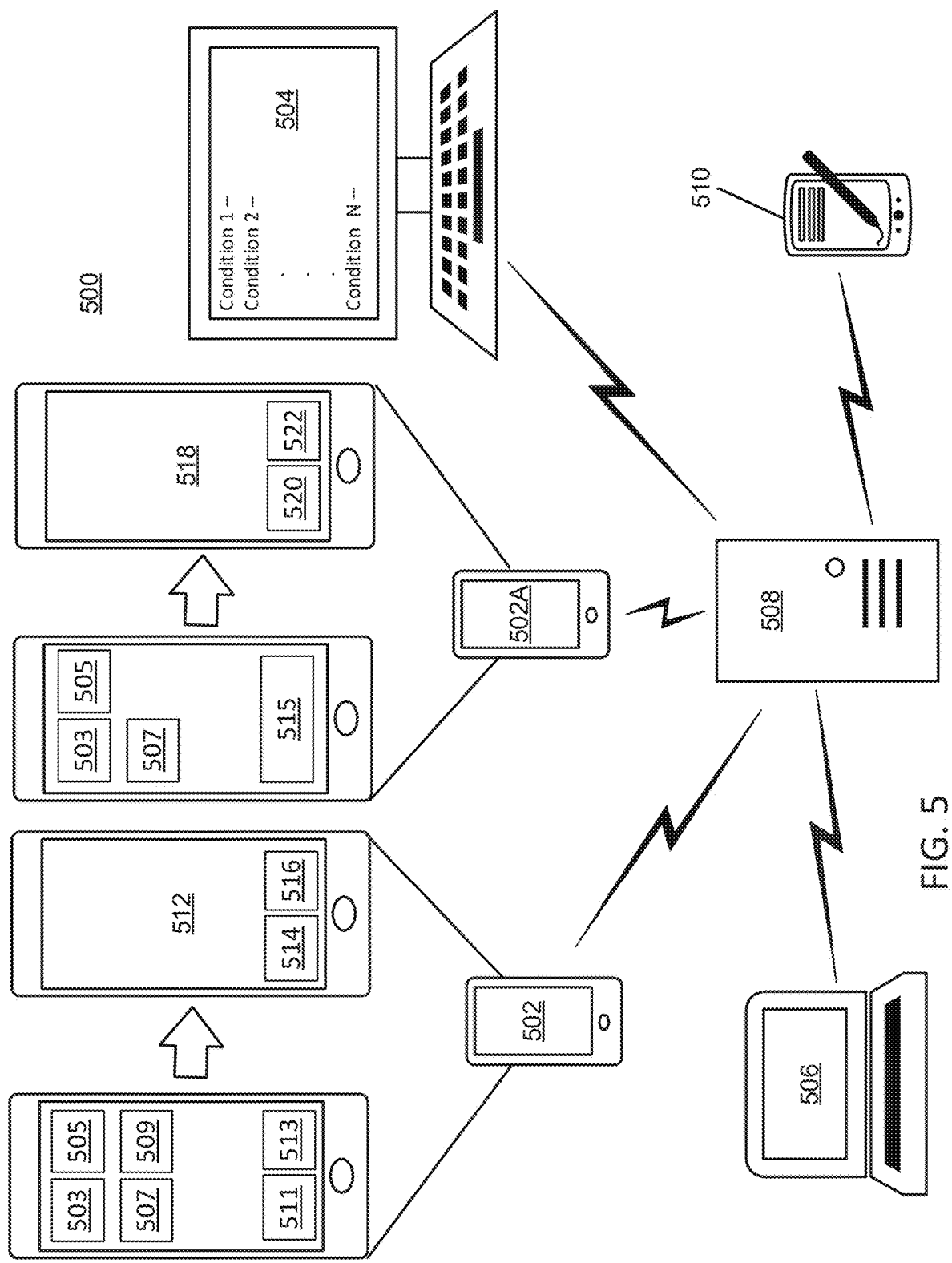
FIG. 5 is a diagram showing a system for creating, updating, and/or controlling access to problem lists for Electronic Health Records, in accordance with embodiments of the present invention.

Referring now to FIG. 5, a diagram showing an exemplary high-level system architecture 500 for creating, updating, and/or controlling access to problem lists (PLs) for Electronic Health Records (EHRs) is illustratively depicted in accordance with embodiments of the present invention.

In an embodiment, a server 508 (e.g., FHIR server, HL7 server, etc.) can include a plurality of stored EHRs for a plurality of patients, and can further be configured for creating, updating, and/or controlling access to PLs for any of the EHRs. In some embodiments, more than one server 508 can be utilized, including as a stand-alone specialized server 508 dedicated to creating, updating, and/or controlling access to PLs for the EHRs, in accordance with aspects of the present invention. The server 508 can determine appropriate customized graphical user interface (GUI) layouts based on, for example, a user's role in an organization (e.g., PMP, TMP, nurse, administrator, etc.), or other layouts or criteria, which can be set by a user with authorization to modify GUI layouts for particular groups.

In an embodiment, authentication of a user and/or device for access to the EHR and/or particular PLs, and a determination of permissions (e.g., access, annotate, approve updates, etc.) for the user and/or device can be executed at the server 508, and the appropriate GUI (including only necessary buttons to minimize screen clutter and improve usability) can be sent from the server 508 to any of a plurality of user devices (e.g., smartphone 502, 502A, desktop computer 504, laptop 506, PDA 510, etc.) and can be customized for optimal use efficiency for any of a plurality of device displays, in accordance with aspects of the present invention.

A portable communication device 502 (e.g., cellular telephone, smartphone device, etc.) is known to have a relatively small screen, which can cause reading a list of options/conditions in a PL to be cumbersome and difficult to read. In accordance with embodiments of the present invention, a GUI can be generated and/or populated with options/conditions presented in a manner which increases usability and/or readability of the questions. In an exemplary embodiment of the present invention, the display screen of the portable communication device 502 can include one or more GUI buttons 503, 505, 507, 509, 511, and 513 corresponding to a profile of a particular healthcare professional (e.g., PMP, TMP, nurse, etc.), which can be generated on any device upon authentication of the healthcare professional and a determination of access to a particular PL for a particular patient and access type (e.g., viewing, annotate, approve updating, etc.) for the user.

In an embodiment, a smartphone 502 can be utilized to authenticate a user (e.g., healthcare professional), and upon determination of access and access type for particular PLs for the user, device, and/or group designation (e.g., PMP, TMP, etc.), can generate a GUI customized for the user, device, and/or group designation with appropriate permissions.

As an illustrative example, assume a smartphone 502 has been utilized to authenticate a user as a PMP, and the permissions of the PMP can include access, annotate, and update approval for any PLs related to a particular patient. In this instance, PMP-level specific buttons can be generated and populated on the screen of the smartphone 502. The buttons can be designated for access to, for example, an MPL 503, WPL 505, CPL 507, and SPL 509, and can further include buttons which can be pressed after selection of the particular PL 503, 505, 507, 509 to provide access to view 511 or annotate/edit 513 the selected PL for the user, in accordance with aspects of the present invention. After selecting the PL, the contents of the PL 512 can be displayed (e.g., on a new screen, as a popup, etc.), and an edit button 514 can be pressed to generate a free form data entry area (e.g., new screen, popup, etc.), and a commit button 516 can be pressed after entering data in 514 to upload the annotated data to a server 508 for verification, approval, and/or updating one or more PLs and/or the EHR upon a determination that the annotated data is appropriate to store in one or more of the PLs and/or the EHR, in accordance with aspects of the present invention.

As a further illustrative example, assume a smartphone 502A has been utilized to authenticate a user as an administrator, and the permissions of the administrator can include access and update approval for only some PLs related to a particular patient. In this instance, administrator-level specific buttons can be generated and populated on the screen of the smartphone 502A. The buttons can be designated for access to, for example, an MPL 503, WPL 505, and CPL 507 (and not the SPL 509), and can further include a button which can be pressed after selection of the particular PL 503, 505, 507 to provide access to view 515 the selected PL for the user, in accordance with aspects of the present invention. After selecting the PL, the contents of the PL 518 can be displayed (e.g., on a new screen, as a popup, etc.), and a request edit capability button 514 can be pressed, which can generate and send a request to a user with approval authority for access to edit the PL. An exit button 522 can be pressed at any time (e.g., before or after viewing the PL, pressing button 520, etc.), in accordance with aspects of the present invention.

It is to be appreciated that the buttons are exemplary, and other buttons and/or GUI functions can be employed in any combination for any type of access, including, for example, access to, for example, viewing an MPL 503, WPL 505, CPL 507, and SPL 509 for a patient, but only edit capability authorized for a user for the MPL 503, WPL 505, and CPL 507. In this instance, the annotate/edit button 513 can be inaccessible (e.g., grayed out, removed, etc.) upon pressing a button for access to a particular PL (e.g., MPL 503, WPL 505, CPL 507, and SPL 509) for which edit access is not authorized for a particular user, in accordance with aspects of the present invention.

In various embodiments of the present invention, a long press/long tap (e.g., employed on touchscreens, smartphones, tablets, smartwatches, etc. to the long press or long tap increases the flexibility of the user interface. The "short press" or "short tap" (releasing right away) performs one operation, while pressing/tapping and holding that same button for a short time activates another) of any of the buttons 503, 505, 507, 509, 511, 513, etc. can bring up further details regarding the pressed button, which can be displayed as a pop-up window 515 (e.g., either being displayed in front of other buttons 503, 505, 507, 509, 511, 513, etc. or next to the buttons), or on a new display screen 512, 516 (e.g., to display further details (e.g., PLs, EHR, etc.) regarding any of the clicked buttons).

In some embodiments, similarly to the customized GUI described above with reference to the portable communication device 502 (e.g., cellular telephone, smartphone, etc.), a personal computer (PC) and/or virtual machine (VM) 504, a laptop computer 506, and/or any type of portable computing device 510 (e.g., personal digital assistant (PDA), tablet, phablet, etc.) can include a similar customizable interface/layout for interacting with the system 500.

In some aspects of the present invention, rather than presenting the options/conditions as shown with reference to the personal communication device 502, the interface can display the options/conditions as an ordered list (e.g., on a single or multiple screens), in separate smaller windows on a computer screen, and/or highlight highly prioritized options/conditions to improve speed and efficiency of presenting and/or answering interview questions for one or more users. For example, the exemplary display screen of the PC 504 can include customizable lists, which can emphasize (e.g., highlight, bold, underline, etc.) particular options/conditions in accordance with various embodiments of the present invention.

In accordance with aspects of the present invention, the GUIs shown in, for example, 502, 502A, 504, 506, and 508 can be customized to quickly and efficiently display the most relevant data for a particular user, task, condition, etc. from a PL and/or EHR for a particular patient. The data can be presented to users (e.g., health care workers) in real-time to aid in, for example, physician decision making regarding particular treatment for particular patients. Thus, the customizable GUIs of the system 500 can reduce the time spent by users (e.g., health care workers) in completing tasks, and increasing the accuracy and efficiency of determination, analysis, and presentation of patient co-morbidities in accordance with various embodiments of the present invention.

Figure 6:
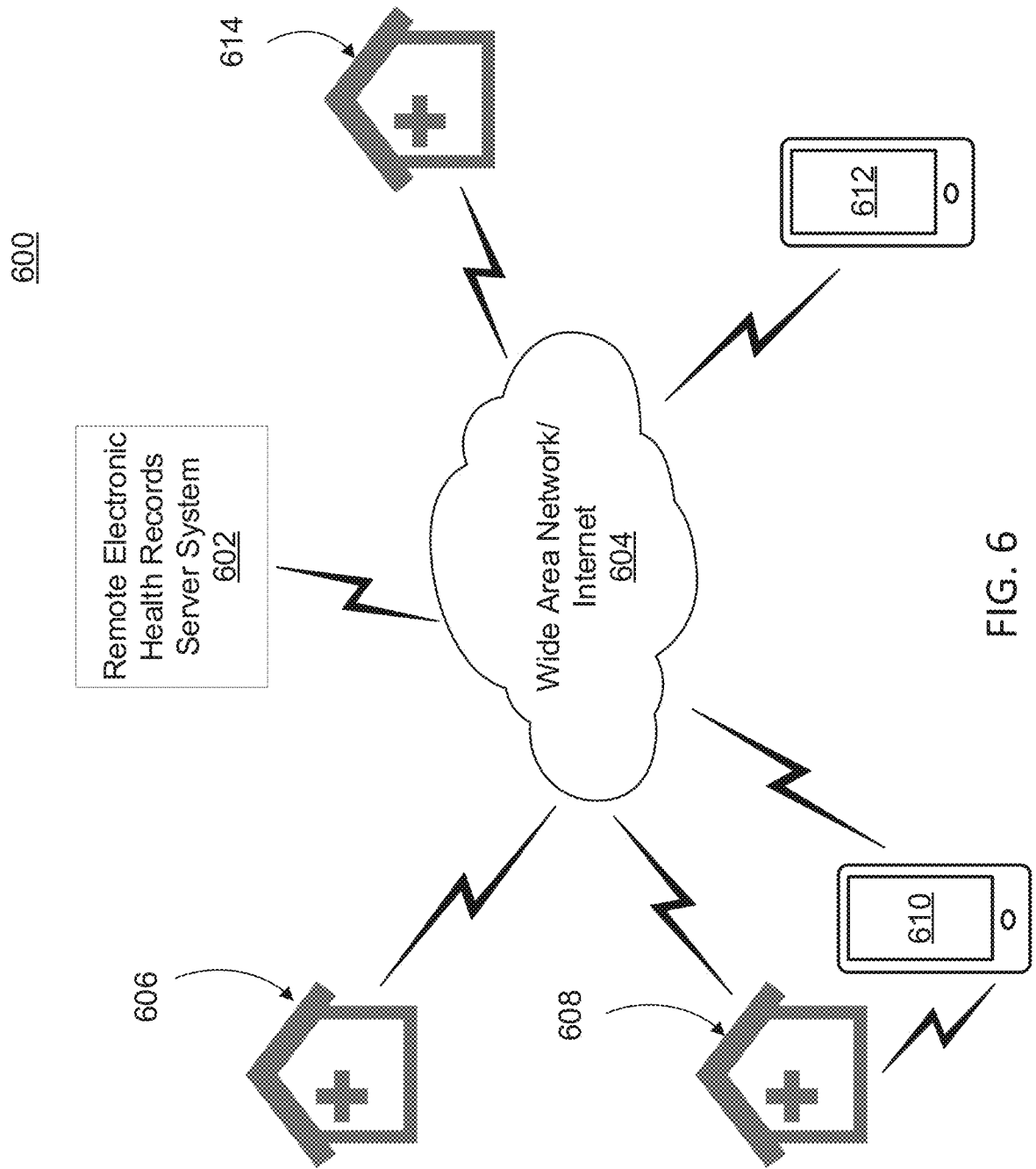
FIG. 6 is a diagram showing a system for creating, updating, and/or controlling access to problem lists for Electronic Health Records for multiple remote sites and/or users, in accordance with embodiments of the present invention.

Referring now to FIG. 6, a diagram showing a system 600 for creating, updating, and/or controlling access to problem lists (PLs) for Electronic Health Records (EHRs) for multiple remote sites and/or users in accordance with embodiments of the present invention.

In an embodiment, a remote EHR server system 602 can be configured for creating, updating, and/or controlling access to PLs for EHRs for one or more patients for multiple remote sites and/or users (e.g., healthcare professionals), in accordance with aspects of the present invention. The EHR server system 602 can be cloud-based and can be connected to one or more healthcare facilities 606, 614, 608 and/or user devices 610, 612, providing access (e.g., viewing, updating, etc.) to real-time updated patient PLs and EHRs based on user and/or device permissions, which can be authenticated by any of a plurality of authentication means, in accordance with aspects of the present invention.

Figure 7:
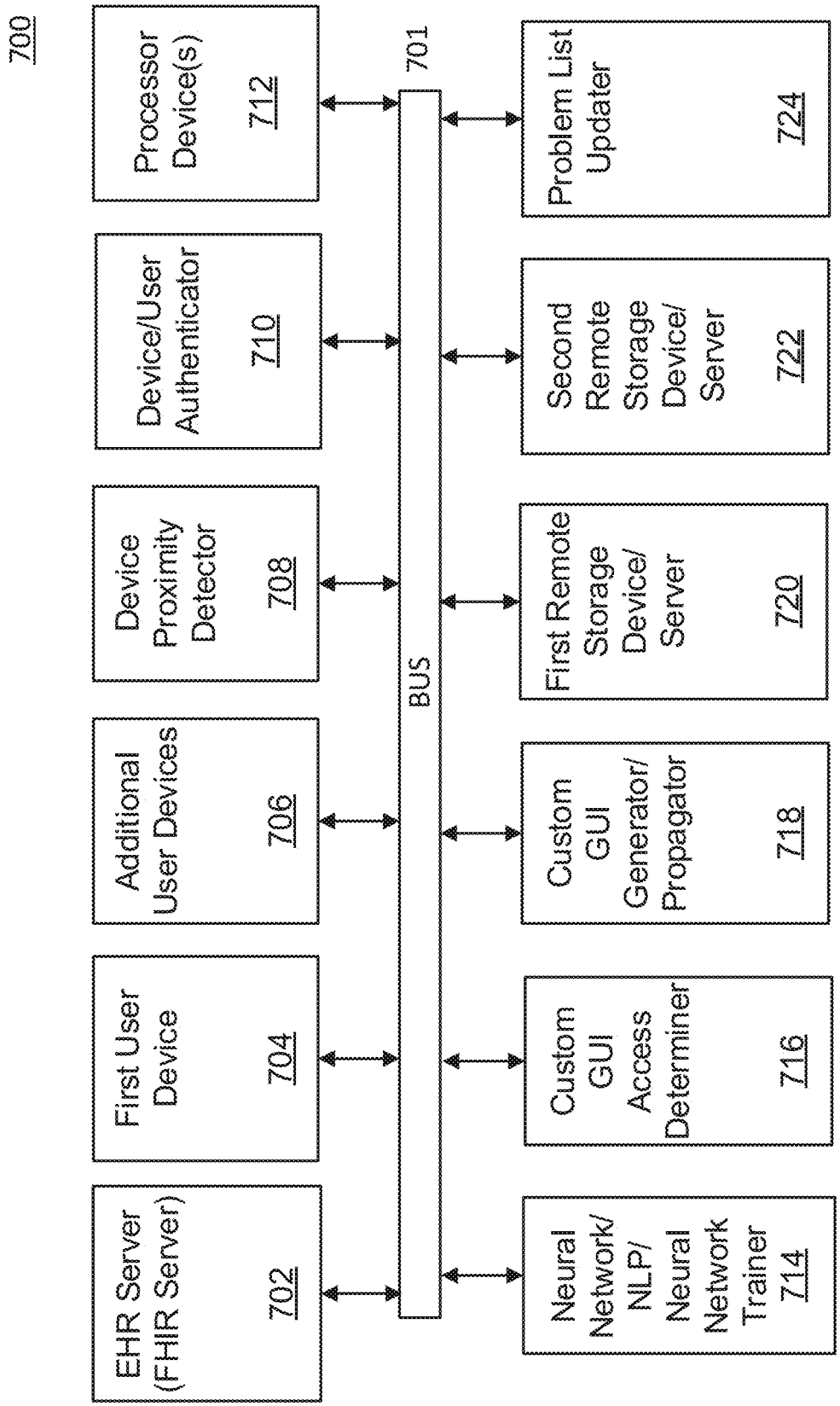
FIG. 7 is a diagram showing a system for creating, updating, and/or controlling access to problem lists for Electronic Health Records, in accordance with embodiments of the present invention.

Referring now to FIG. 7, a diagram showing a system 700 for creating, updating, and/or controlling access to problem lists (PLs) for Electronic Health Records (EHRs) is illustratively depicted in accordance with embodiments of the present invention.

In accordance with various embodiments of the present invention, an EHR server 702 (e.g., Fast Healthcare Interoperability Resources (FHIR) server, Health Level Seven Messaging Standard (HL7) server, etc.) can be employed for storing, receiving, distributing, and/or controlling access to the server 702 and/or data stored on the server 702. A first user device 704 and any number of a plurality of user devices 706 can be utilized to access the server 702 upon authentication of a user and/or user device 704, 706. In some embodiments, authentication of a user and/or user device 704, 706 can be performed using device proximity sensors/detectors 708, which can enable authenticated access to the server 702 based on a position of a device 704, 706 relative to the device proximity sensors/detectors 706. The device proximity sensors/detectors 706 can be configured to restrict access from a device 704, 706 according to any boundary desired by a user (e.g., restricted to a hospital campus, building, floor, department, room, etc.), in accordance with aspects of the present invention.

In some embodiments, verification of a user and/or user device can be performed by a device/user authenticator 710 based on an assigned category for a device 704, 706 and/or the contents of a stored profile for one or more healthcare professionals, which can include a specialty, job title, department, etc., in accordance with aspects of the present invention. For example, the device/user authenticator 710 can assign EHR permissions (e.g., particular PL annotation, viewing, approving updates, etc.) based on designations of specialty (e.g., Emergency Room Physician, Surgeon, Anesthesiologist, etc.) and/or responsibilities designated for particular groups by a particular medical facility. One or more processor devices 712 can be employed for executing various aspects of the present invention, and can be connected by a bus 701 or any other suitable connection means (e.g., wired, wireless, cloud-based, etc.), in accordance with embodiments of the present invention.

In some embodiments, a neural network 714 can be trained for natural language/unstructured data processing to pull data from unstructured annotations (e.g., PL annotations). The trained neural network 714 can detect duplicate and/or non-duplicate entries into any of a plurality of PLs received as natural language from annotated PLs, and can remove duplicate entries and/or add new entries (e.g., categories, diseases, etc.) from one or more PLs upon a determination by the problem list editor/updater 724 that the annotated data, categories, etc. is appropriate to add and/or remove from one or more of a plurality of hierarchical PLs (e.g., MPL, WPL, SPL, CPL, etc.), in accordance with aspects of the present invention. In some embodiments, the problem list updater/editor 724 utilizes algorithms to determine and assign access for particular medical professionals to different hierarchical levels of the plurality of PLs.

In an embodiment, such algorithms can be based on the credentialling categories at a particular medical facility. These categories can be input and correlated (e.g., using a permission table) at a server (e.g., remote server), and access can be granted or denied to particular PLs based on where particular users and/or PLs are in the hierarchy of PLs. For example, an algorithm may have to determine existing and/or generate new categories of medical staff membership and/or PL content to regulate the limits of assignment (e.g., a probationary attending physician or nurse may not be allowed to be assigned PMP responsibilities), and if an impermissible assignment is requested, such an assignment will not be permitted to be entered into the system and/or an alert to one or more users can be transmitted notifying the user that the request has been denied, in accordance with aspects of the present invention.

In some embodiments, a custom graphical user interface (GUI) access determiner 716 can interface with the problem list updater/editor 724 and the authenticator 710 to provide an appropriate GUI for different types of medical professionals and/or individual users based on their organizational role (e.g., PMP, TMP, nurse, administrator, consultant, etc.), physical location, and/or any of a plurality of user-set access categories, and once an appropriate GUI is determined, a custom GUI generator/propagator 718 can push the determined appropriate GUI to a user device based on the determination. The GUIs generated can have different buttons and/or functionality depending on the access determined by the GUI access determiner 716, in accordance with aspects of the present invention. A first remote storage device 720 and/or a second (or more) remote storage device 722 can be employed for receiving and/or storing data from one or more of the user devices 704, 706, and can be interconnected with the servers 702 for updating the PLs and EHRs in real time from one or more healthcare facilities, in accordance with aspects of the present invention.

In the embodiment shown in FIG. 7, the elements thereof are interconnected by a bus 701. However, in other embodiments, other types of connections can also be used. Moreover, in an embodiment, at least one of the elements of system 700 is processor-based and/or a logic circuit. Further, while one or more elements may be shown as separate elements, in other embodiments, these elements can be combined as one element. The converse is also applicable, where while one or more elements may be part of another element, in other embodiments, the one or more elements may be implemented as standalone elements. These and other variations of the elements of system 700 are readily determined by one of ordinary skill in the art, given the teachings of the present principles provided herein, while maintaining the spirit of the present principles.

In accordance with various embodiments, the novel system and method of the present invention can enhance work-flow in the emergency room, or other medical department or facility, and/or multiple facilities with multiple healthcare professionals attending to a particular patient. The inventive system and method can be performed in real time and/or any of a plurality of times, including at time of emergency room disposition, such as during admission, during discharge from the emergency room, during long-term care, during discharge from an inpatient facility, etc., in accordance with aspects of the present invention. The method can be performed multiple times for a single patient, if appropriate. Each time the system is run and/or the method is performed, physician documentation supporting medical decision making can be produced via interpretation of data and findings. This documentation can populate the patient's EHR and/or PLs in real time upon a determination that updating with annotated PL data is appropriate, and be stored for subsequent use, and accordance with aspects of the present invention.

Referring now to FIG. 8, a diagram showing a method 800 for authenticating and applying appropriate access and storage permissions for users and/or devices for creating, updating, and/or controlling access to problem lists (PLs) for Electronic Health Records (EHRs) is illustratively depicted in accordance with embodiments of the present invention.

In an embodiment, a user and/or user device can be authenticated for access and/or editing authorization for one or more hierarchical PLs from a plurality of different PLs in block 802. The authentication can be performed by one or more of a plurality of authentication methods, including, but not limited to, password-based authentication, multi-factor authentication, certificate-based authentication, biometric authentication, Internet of Things (IoT) authentication, token-based authentication, single sign-on, proximity-based authentication, computer-recognition authentication, etc., in accordance with various embodiments of the present invention. A selection of a type of authentication method can be based on a number of factors, including, for example, sensitivity level of data, location of user, hardware available at a facility, etc. in accordance with various aspects of the present invention.

In some embodiments, in block 804, it can be determined whether the user and/or user device has appropriate permissions to view a particular master problem list (MPL) for a particular patient by, for example, a Problem List (PL) annotation authority (which can automatically assign EHR permissions to perform PL annotations based on Medical Staff designations (e.g., PMP, TMP, nurse, etc.) of, for example, specialty and/or responsibility as determined and/or implemented by a particular medical staff office at a particular medical facility, in accordance with various aspects of the present invention.

In some embodiments, if a user and/or user device is determined to have the appropriate permissions to view the MPL in block 804, it can be determined whether the user and/or user device has the appropriate permissions to edit the MPL in block 814. If a user and/or user device is determined to not have the appropriate permissions to view the MPL in block 804 and/or edit the MPL in block 814, authentication of the user and/or user device for viewing a next-level (e.g., higher or lower level) hierarchical derivative problem list (DPL) (e.g., working problem list (WPL)) can be executed in block 806, in accordance with various aspects of the present invention.

If a user and/or user device is determined to have the appropriate permissions to view the WPL in block 806, it can be determined whether the user and/or user device has the appropriate permissions to edit the WPL in block 816. If a user and/or user device is determined to not have the appropriate permissions to view the WPL in block 806 and/or edit the WPL in block 816, authentication of the user and/or user device for viewing a next-level (e.g., higher or lower level) hierarchical DPL (e.g., specialty problem list (SPL)) can be executed in block 808, in accordance with various aspects of the present invention.

If a user and/or user device is determined to have the appropriate permissions to view the SPL in block 808, it can be determined whether the user and/or user device has the appropriate permissions to edit the SPL in block 818. If a user and/or user device is determined to not have the appropriate permissions to view the SPL in block 808 and/or edit the SPL in block 818, authentication of the user and/or user device for viewing a next-level (e.g., higher or lower level) hierarchical DPL (e.g., custom problem list (CPL)) can be executed in block 810, in accordance with various aspects of the present invention.

If a user and/or user device is determined to have the appropriate permissions to view the CPL in block 810, it can be determined whether the user and/or user device has the appropriate permissions to edit the CPL in block 820. If a user and/or user device is determined to not have the appropriate permissions to view the CPL in block 810 and/or edit the CPL in block 820, determined permissions can be sent to a server (e.g., remote EHR server) to generate a customized GUI for individual authenticated users and/or user devices based on the determined permissions in block 822. In block 822, a customized GUI can be generated and the generated GUI can be populated to particular users and/or user devices in real time for immediate access by other appropriate users and/or user devices to provide real-time updated medical information for a patient for a plurality of users who are providing medical services to a patient, in accordance with aspects of the present invention.

In various embodiments, such determination of permissions and generation of a customized GUI can be performed at a remote server (e.g., remote EHR server, FHIR server, etc.), a local desktop computer, and/or a portable computing device (e.g., smartphone, tablet, PDA, etc.), in accordance with aspects of the present invention. Similarly, the content filtering and/or sorting (discussed in further detail herein-below) can be performed at a remote server (e.g., remote EHR server, FHIR server, etc.), a local desktop computer, and/or a portable computing device (e.g., smartphone, tablet, PDA, etc.), in accordance with various embodiments of the present invention.

In some embodiments, once appropriate permissions have been granted, a user can edit one or more PLs for which the user has editing permissions, and the edits/annotations can be received at a remote server (e.g., EHR server) via any known data transmission means in block 824 in accordance with aspects of the present invention. Upon receipt of the edits/annotations to one or more PLs at the server, an alert can be sent to a user and/or user device with approval authority (e.g., PMP, TMP, etc.) for annotations to be added to the EHR, and updates to the PL or higher hierarchical levels (e.g., MPL, WPL, etc.) can be prevented from being stored to the remote server until the edits have been approved for storage in one or more PLs by the user and/or user device with approval authority. In some embodiments, in block 826, update buttons for the PL which has been edited/annotated are disabled (e.g., grayed out, removed, obscured, etc.) on the device screen of the user who entered the edits/annotations until the previously sent edit/annotation updates have been approved or denied by a user and/or user device with approval authority for storage at the remote server, in accordance with aspects of the present invention.

In block 828, it can be determined whether one or more PLs from a plurality of PLs stored on a remote server is required to be updated based on the edits/annotations to the particular PL by a user. Natural language processing (NLP) can be utilized to detect keywords which can be utilized to determine whether the updates should be stored on the server in one or more of the lists (e.g., MPL, WPL, SPL, CPL, etc.), in accordance with embodiments of the present invention. In some embodiments, this NLP can be performed by a local device (e.g., smartphone, tablet, personal computer, etc.) to increase transmission speed and network capability by minimizing the data sent from a user device to a server by associating the edits/annotations with keywords and sending only the keyword data to the remote server. This improves speed and accuracy of categorizing and sorting into particular PLs at the server over conventional EHR updating systems, which do not execute any such functions locally prior to transmitting data to a remote server for verification and hierarchical storage in one or more stored PLs, in accordance with aspects of the present invention.

In block 830, edits/annotations to one or more PLs can be updated at the server and stored upon approval by a user and/or user device with approval authority. In some embodiments, such updates to the PLs can be performed automatically for each PL after approval has been received at the server, and a determination of the type of data included in each of the PLs can be predetermined (e.g., based on historical medical history of a patient, common notations for particular diseases, medical specialty, or department, etc.). In other embodiments, PLs can be created by an end user with customized rules for sorting PLs in block 830 in accordance with aspects of the present invention.

In block 832, updates which have been approved for storage in one of more PLs at the remote server can be populated in real-time to users and/or user devices which have the appropriate hierarchical permissions for particular PLs upon logging into any personal computing device. In accordance with embodiments of the present invention, this real-time receiving of data, sorting, approving, and transmitting updates only to appropriate PLs ensures that any medical professional working on a particular patient has the most current information to treat a patient, as opposed to conventional systems which perform updates to EHR records during off-peak hours to avoid overutilizing network resources and computing power, and thus do not present the most current information regarding a patient to medical professionals providing care to a patient. It is to be appreciated that although the only PLs discussed above are MPL, WPL, SPL, and CPL, any sort of PL can be created and utilized, and further any user category can be created for particular groups of people (e.g., doctor, nurse, orderly, etc.) in accordance with various aspects of the present invention.

In some embodiments, a data transmission and storage policy for storing updates to the EHR in a centralized remote server can be implemented based on the hierarchical levels and permissions determined in block 804. In block 832, a data transmission and storage policy can be predetermined or can be set by a user in accordance with various embodiments of the present invention. As an illustrative example, upon entering data into a user device by a user with access and edit permissions for all of the above-mentioned PLs (which are intended to be illustrative and not limited to only these types of PLs), a policy can be set to send only a portion of the data entered from a user device to a server after using NLP to transform the data entered into a keyword or keywords, and determining if the keyword associated with the updated data is appropriate to sort into an existing category. If yes, then the keywords can be added to an existing category, and if no, then the keywords can be utilized to form a new category for one or more PLs, in accordance with aspects of the present invention.

Figure 9:
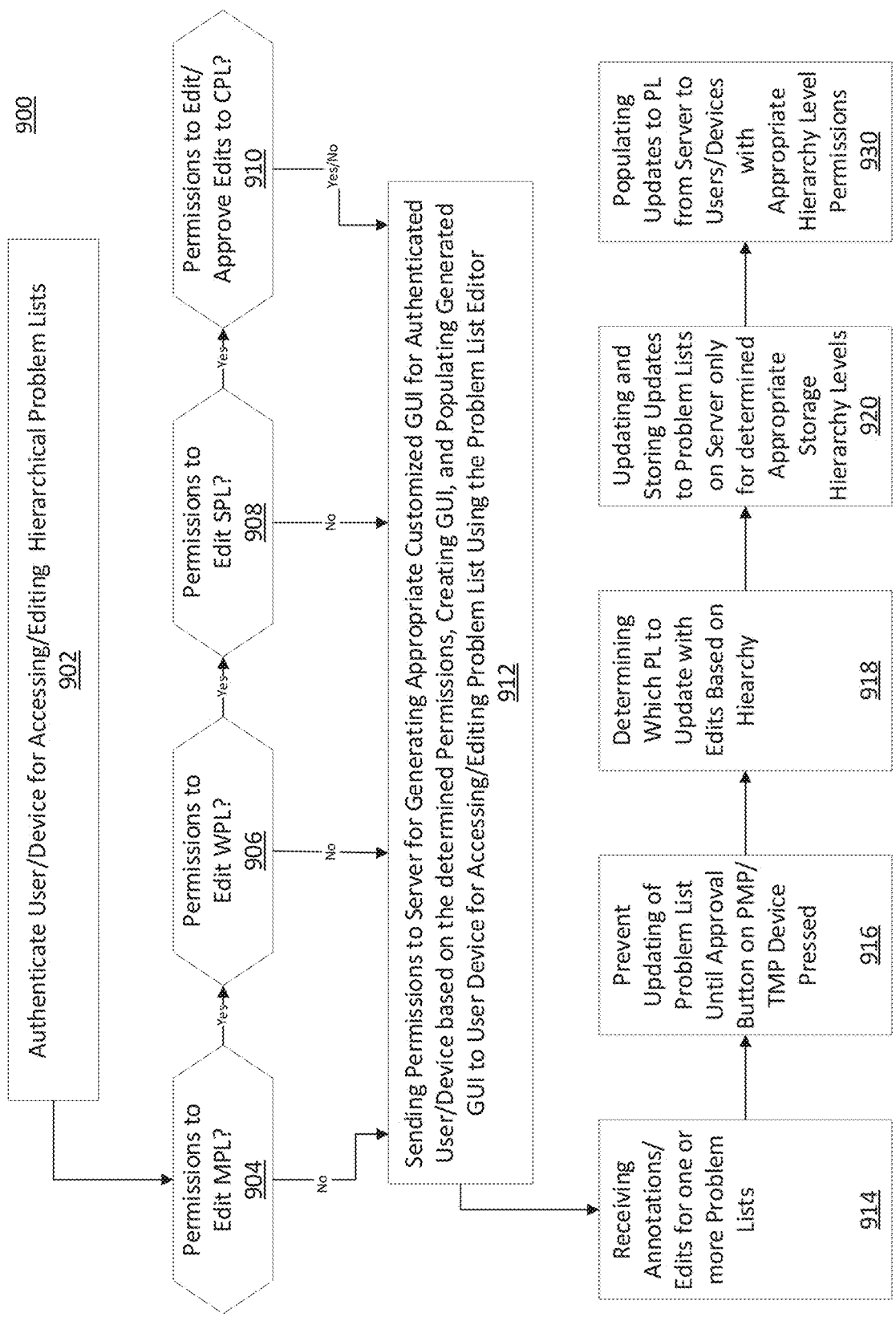
FIG. 9 is a diagram showing a method for authenticating and applying appropriate access and storage permissions for users and/or devices for creating, updating, and/or controlling access to problem lists for Electronic Health Records, in accordance with embodiments of the present invention.

Referring now to FIG. 9, a diagram showing a method 900 for authenticating and applying appropriate access and storage permissions for users and/or devices for creating, updating, and/or controlling access to problem lists (PLs) for Electronic Health Records (EHRs) is illustratively depicted in accordance with embodiments of the present invention.

In some embodiments, a user and/or user device can be authenticated for access and/or editing authorization for one or more hierarchical PLs from a plurality of different PLs in block 902. In an illustrative embodiment, it can be assumed that all authenticated users have view permission for all PLs stored at a remote server, and it can be determined which of a plurality of authenticated users have the appropriate permissions to edit particular PLs, as will be described in further detail herein below. The authentication can be performed by one or more of a plurality of authentication methods, including, but not limited to, password-based authentication, multi-factor authentication, certificate-based authentication, biometric authentication, Internet of Things (IoT) authentication, token-based authentication, single sign-on, proximity-based authentication, computer-recognition authentication, etc., in accordance with various embodiments of the present invention. A selection of a type of authentication method can be based on a number of factors, including, for example, sensitivity level of data, location of user, hardware available at a facility, etc. in accordance with various aspects of the present invention.

In some embodiments, a determination of whether a user and/or user device has appropriate permissions to edit a particular PL can be made in a hierarchical manner beginning with a MPL in block 904.

In some embodiments, in block 904, it can be determined whether the user and/or user device has appropriate permissions to view a particular MPL for a particular patient by, for example, a PL annotation authority (which can automatically assign EHR permissions to perform PL annotations based on Medical Staff designations (e.g., PMP, TMP, nurse, etc.) of, for example, specialty and/or responsibility as determined and/or implemented by a particular medical staff office at a particular medical facility, in accordance with various aspects of the present invention. If a user and/or user device is determined to have the appropriate permissions to edit the MPL in block 904, it can then proceed along the hierarchical PLs to determine whether a user and/or user device has appropriate permissions to edit a WPL for the patient in block 906. If yes, it can be determined whether a user and/or user device has appropriate permissions to edit a SPL for the patient in block 908. If yes, it can be determined whether a user and/or user device has appropriate permissions to edit a CPL for the patient and whether the user and/or user device has appropriate permissions to approve edits to the MPL, WPL, SPL, and or CPL in block 910, in accordance with aspects of the present invention.

In some embodiments, if a user and/or user device is determined to not have the appropriate permissions to edit a PL in blocks 904, 906, 908, or 904, any determined permissions can be sent to a server (e.g., remote EHR server) to generate a customized GUI for individual authenticated users and/or user devices based on the determined permissions in block 912. In block 912, a customized GUI can be generated and the generated GUI can be populated to particular users and/or user devices in real time for immediate access by other appropriate users and/or user devices to provide real-time updated medical information for a patient for a plurality of users who are providing medical services to a patient, in accordance with aspects of the present invention.

In various embodiments, such determination of permissions and generation of a customized GUI can be performed at a remote server (e.g., remote EHR server, FHIR server, etc.), a local desktop computer, and/or a portable computing device (e.g., smartphone, tablet, PDA, etc.), in accordance with aspects of the present invention. Similarly, the content filtering and/or sorting (discussed in further detail hereinbelow) can be performed at a remote server (e.g., remote EHR server, FHIR server, etc.), a local desktop computer, and/or a portable computing device (e.g., smartphone, tablet, PDA, etc.), in accordance with various embodiments of the present invention.

In some embodiments, once appropriate permissions have been granted, a user can edit one or more PLs for which the user has editing permissions, and the edits/annotations can be received at a remote server (e.g., EHR server) via any known data transmission means in block 914 in accordance with aspects of the present invention. Upon receipt of the edits/annotations to one or more PLs at the server, an alert can be sent to a user and/or user device with approval authority (e.g., PMP, TMP, etc.) for annotations to be added to the EHR, and updates to the PL or higher hierarchical levels (e.g., MPL, WPL, etc.) are prevented from being stored to the remote server until the edits have been approved for storage in one or more PLs by the user and/or user device with approval authority in block 916. In some embodiments, in block 916, update buttons for the PL which has been edited/annotated are disabled (e.g., grayed out, removed, obscured, etc.) on the device screen of the user who entered the edits/annotations until the previously sent edit/annotation updates have been approved or denied by a user and/or user device with approval authority for storage at the remote server, in accordance with aspects of the present invention.

In block 918, it can be determined whether one or more PLs from a plurality of PLs stored on a remote server is required to be updated based on the edits/annotations to the particular PL by a user. Natural language processing (NLP) can be utilized to detect keywords which can be utilized to determine whether the updates should be stored on the server in one or more of the lists (e.g., MPL, WPL, SPL, CPL, etc.), in accordance with embodiments of the present invention. In some embodiments, this NLP can be performed by a local device (e.g., smartphone, tablet, personal computer, etc.) to increase transmission speed and network capability by minimizing the data sent from a user device to a server by associating the edits/annotations with keywords and sending only the keyword data to the remote server. This improves speed and accuracy of categorizing and sorting into particular PLs at the server over conventional EHR updating systems, which do not execute any such functions locally prior to transmitting data to a remote server for verification and hierarchical storage in one or more stored PLs, in accordance with aspects of the present invention.

In block 920, edits/annotations to one or more PLs can be updated at the server and stored upon approval by a user and/or user device with approval authority. In some embodiments, such updates to the PLs can be performed automatically for each PL after approval has been received at the server, and a determination of the type of data included in each of the PLs can be predetermined (e.g., based on historical medical history of a patient, common notations for particular diseases, medical specialty, or department, etc.). In other embodiments, PLs can be created by an end user with customized rules for sorting PLs in block 920 in accordance with aspects of the present invention.

In block 930, updates which have been approved for storage in one of more PLs at the remote server can be populated in real-time to users and/or user devices which have the appropriate hierarchical permissions for particular PLs upon logging into any personal computing device. In accordance with embodiments of the present invention, this real-time receiving of data, sorting, approving, and transmitting updates only to appropriate PLs ensures that any medical professional working on a particular patient has the most current information to treat a patient, as opposed to conventional systems which perform updates to EHR records during off-peak hours to avoid overutilizing network resources and computing power, and thus do not present the most current information regarding a patient to medical professionals providing care to a patient. It is to be appreciated that although the only PLs discussed above are MPL, WPL, SPL, and CPL, any sort of PL can be created and utilized, and further any user category can be created for particular groups of people (e.g., doctor, nurse, orderly, etc.) in accordance with various aspects of the present invention.

In some embodiments, a data transmission and storage policy for storing updates to the EHR in a centralized remote server can be implemented based on the hierarchical levels and permissions determined in blocks 904, 906, 908, and/or 910. In block 930, a data transmission and storage policy can be predetermined or can be set by a user in accordance with various embodiments of the present invention. As an illustrative example, upon entering data into a user device by a user with access and edit permissions for all of the above-mentioned PLs (which are intended to be illustrative and not limited to only these types of PLs), a policy can be set to send only a portion of the data entered from a user device to a server after using NLP to transform the data entered into a keyword or keywords, and determining if the keyword associated with the updated data is appropriate to sort into an existing category. If yes, then the keywords can be added to an existing category, and if no, then the keywords can be utilized to form a new category for one or more PLs, in accordance with aspects of the present invention.

It is to be appreciated that although the hierarchical PLs described herein are limited for ease of illustration to a Master Problem List (MPL), a Working Problem List (WPL), a Specialty Problem List (SPL), and a Custom Problem List (CPL), any sort of hierarchical PLs can be generated, populated with data from a patient, and an appropriate position in the hierarchical PLs for the patient can be determined based on determined permissions for particular medical facilities correlated with credentialing practices of the medical facilities, in accordance with various embodiments of the present invention.

For example, a SPL level can be generated specifically to contain that level of PL data, and the groups can be assigned based on the credentials of particular medical professionals, departments, sections, etc. to limit access to particular PLs. In large facilities (e.g., a hospital with multiple specialists working on a particular patient) or consolidated medical staffs, it is likely that more than one member of a specialty group will make entries into the SPL during a patient visit, and thus, individual medical professionals within the specialty group may create a new PL (e.g., CPL) that is more appropriate for their personal use, and this PL can be added automatically into the hierarchy based on credentials and determined permissions for the new PL, in accordance with aspects of the present invention.

Having described preferred embodiments of a system and method for creating, updating, filtering, and/or controlling access to problem lists for Electronic Health Records (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims.

What is claimed is:

1. An electronic health records (EHR) system, comprising:
a server comprising a medical records database stored in a computer-readable storage medium operatively coupled to at least one processor device, the processor device being configured for:
receiving requests for medical data for a patient in a master problem list (MPL) from one or more user devices;
authenticating one or more users and user devices using multi-factor authentication prior to granting access to the MPL, and, upon successful authentication, determining and granting the authenticated user devices appropriate list permissions for one or more of a plurality of hierarchical derivative problem lists (DPLs);
implementing a temporal-based data transmission and storage policy that is predetermined or set by a user, the implementing comprising transforming entered data into one or more keywords using natural language processing (NLP) and sending only the keywords from a user device to a server to minimize an amount of data transmitted to the server during updating the MPL during peak usage times;
determining and granting one or more of the user devices appropriate list permissions for one or more of a plurality of hierarchical derivative problem lists (DPLs) based on the authenticating and the data transmission and storage policy;
receiving, at the server, annotated data related to the patient from one or more of the user devices based on annotations made to one or more of the DPLs; and
updating, in real-time at the server, one or more hierarchical problem lists (PLs), each including two or more PL levels, with the received annotated data from the one or more user devices, the updating comprising:
comparing, by the server, the received annotated data with current entries in the MPL using natural language processing (NLP) to categorize updates and identify duplicate entries;
iteratively detecting and removing the identified duplicate entries from the MPL and storing non-duplicate entries in appropriate authorized DPLs based on the NLP and hierarchical list update permissions for each of the DPLs; and
increasing transmission speed and real-time network capability for the updating by the server by minimizing an amount of data transmitted by the one or more user devices to the server during the updating by associating edits in the annotated data with one or more keywords and transmitting only data for the keywords to the server for the updating the one or more PLs, in accordance with the implemented data transmission and storage policy;
sending an alert to at least one of a user or user device with approval authority for annotations to be added to the EHR, wherein updates to higher hierarchical levels are prevented from being stored to the server until the edits have been approved for storage in one or more PLs by the at least one of a user or user device with approval authority; and
disabling update buttons for the PL which has been edited/annotated on the device screen of the user who entered the edits/annotations until the previously sent edit/annotation updates have been approved or denied by a user and/or user device with approval authority for storage at the remote server.

2. The system of claim 1, wherein the processor is further configured for generating and associating one or more non-duplicate PL categories corresponding to the non-duplicate entries for storage of the non-duplicate entries.

3. The system of claim 2, wherein the processor is further configured for generating an encoded string identifier representative of the non-duplicate PL categories for increased speed of updating, retrieval, and population of the annotated data across a computing network.

4. The system of claim 3, wherein the generated encoded string identifier comprises a generated hash function.

5. The system of claim 1, further comprising encrypting and sending the annotated PLs for the patient from the MPL stored on the server to users authorized for access to particular PLs from the plurality of PLs for the patient.

6. The system of claim 1, wherein the PLs are updated in a hierarchical manner such that each PL level prevents automatic uploading to the server upon entry of new data from a lower-level PL until verification by a designated user that higher level PLs includes appropriate access and storage permissions for the new data.

7. The system of claim 1, wherein the plurality of DPLs includes at least one of a Working Problem List (WPL), a Specialty Problem List (SPL), or a Custom Problem List (CPL), wherein the WPL is an index of active medical problems, the SPL is a problem list generated by and specific to a specialized medical field, and the CPL is a list created by and specific to a particular user, the user being a medical clinician.

8. The system of claim 7, wherein new medical data entered into the CPL is stored on a mobile device of the user, and only medical data from the new medical data which is related to categories already present in the hierarchical problem lists MPL, WPL, and SPL is uploaded to each of the hierarchical problem lists MPL, WPL, and SPL, respectively, and stored in the server.

9. A method for maintaining an electronic health records (EHR) system, comprising:
   storing a medical records database in a computer-readable storage medium operatively coupled to at least one processor device;
   receiving requests for medical data for a patient in a master problem list (MPL) from one or more user devices;
   authenticating one or more users and user devices using multi-factor authentication prior to granting access to the MPL, and, upon successful authentication, determining and granting the authenticated user devices appropriate list permissions for one or more of a plurality of hierarchical derivative problem lists (DPLs);
   implementing a temporal-based data transmission and storage policy that is predetermined or set by a user, the implementing comprising transforming entered data into one or more keywords using natural language processing (NLP) and sending only the keywords from a user device to a server to minimize an amount of data transmitted to the server during updating the MPL during peak usage times;
   determining and granting one or more of the user devices appropriate list permissions for one or more of a plurality of hierarchical derivative problem lists (DPLs) based on the authenticating and the data transmission and storage policy;
   receiving at a server annotated data related to the patient from one or more of the one or more user devices based on annotations made to one or more of the DPLs; and
   updating, in real time at the server, one or more hierarchical problem lists (PLs), each including two or more PL levels, with the received annotated data from the one or more user devices, the updating comprising:
      comparing, by the server, the received annotated data with current entries in the MPL using natural language processing (NLP) to categorize updates and identify duplicate entries;
      iteratively detecting and removing the identified duplicate entries from the MPL and storing non-duplicate entries in appropriate authorized DPLs based on the NLP and hierarchical list update permissions for each of the DPLs;
      increasing transmission speed and real-time network capability for the updating by the server by minimizing an amount of data transmitted by the one or more user devices to the server during the updating by associating edits in the annotated data with one or more keywords and transmitting only data for the keywords to the server for the updating the one or more PLs, in accordance with the implemented data transmission and storage policy;
      sending an alert to at least one of a user or user device with approval authority for annotations to be added to the EHR, wherein updates to higher hierarchical levels are prevented from being stored to the server until the edits have been approved for storage in one or more PLs by the at least one of a user or user device with approval authority; and
      disabling update buttons for the PL which has been edited/annotated on the device screen of the user who entered the edits/annotations until the previously sent edit/annotation updates have been approved or denied by a user and/or user device with approval authority for storage at the remote server.

10. The method of claim 9, wherein the processor is further configured for generating and associating one or more non-duplicate PL categories corresponding to the non-duplicate entries for storage of the non-duplicate entries.

11. The method of claim 10, wherein the processor is further configured for generating an encoded string identifier representative of the non-duplicate PL categories for increased speed of updating, retrieval, and population of the annotated data across a computing network.

12. The method of claim 11, wherein the generated encoded string identifier comprises a generated hash function.

13. The method of claim 9, further comprising encrypting and sending the annotated PLs for the patient from the MPL stored on the server to users authorized for access to particular PLs from the plurality of PLs for the patient.

14. The method of claim 9, wherein the PLs are updated in a hierarchical manner such that each PL level prevents automatic uploading to the server upon entry of new data from a lower-level PL until verification by a designated user that higher level PLs includes appropriate access and storage permissions for the new data.

15. The method of claim 9, wherein the plurality of DPLs includes at least one of a Working Problem List (WPL), a Specialty Problem List (SPL), or a Custom Problem List (CPL), the WPL being an index of active medical problems, the SPL being a problem list generated by and specific to a specialized medical field, and the CPL being a list created by and specific to a particular user, the user being a medical clinician.

16. The method of claim 15, wherein new medical data entered into the CPL is stored on a mobile device of the user, and only medical data from the new medical data which is related to categories already present in the hierarchical problem lists MPL, WPL, and SPL is uploaded to each of the hierarchical problem lists MPL, WPL, and SPL, respectively, and stored in the server.

17. A non-transitory computer readable storage medium comprising a computer readable program operatively coupled to at least one processor device for maintaining an electronic health records (EHR) system, wherein the computer readable program when executed on a computer causes the computer to perform steps of:
   storing a medical records database in a computer-readable storage medium operatively coupled to the at least one processor device;
   receiving requests for medical data for a patient in a master problem list (MPL) from one or more user devices;
   authenticating one or more users and user devices using multi-factor authentication prior to granting access to the MPL, and, upon successful authentication, determining and granting the authenticated user devices appropriate list permissions for one or more of a plurality of hierarchical derivative problem lists (DPLs);

implementing a temporal-based data transmission and storage policy that is predetermined or set by a user, the implementing comprising transforming entered data into one or more keywords using natural language processing (NLP) and sending only the keywords from a user device to a server to minimize an amount of data transmitted to the server during updating the MPL during peak usage times;

determining and granting one or more of the user devices appropriate list permissions for one or more of a plurality of hierarchical derivative problem lists (DPLs) based on the authenticating and the data transmission and storage policy;

receiving at a server annotated data related to the patient from one or more of the one or more user devices based on annotations made to one or more of the DPLs; and updating, in real time at the server, one or more hierarchical problem lists (PLs), each including two or more PL levels, with the received annotated data from the one or more user devices, the updating comprising:

comparing, by the server, the received annotated data with current entries in the MPL using natural language processing (NLP) to identify duplicate entries;

iteratively detecting and removing the identified duplicate entries from the MPL and storing non-duplicate entries in appropriate authorized DPLs based on the NLP and hierarchical list update permissions for each of the DPLs;

increasing transmission speed and real-time network capability for the updating by the server by minimizing an amount of data transmitted by the one or more user devices to the server during the updating by associating edits in the annotated data with one or more keywords and transmitting only data for the keywords to the server for the updating the one or more PLs, in accordance with the implemented data transmission and storage policy;

sending an alert to at least one of a user or user device with approval authority for annotations to be added to the EHR, wherein updates to higher hierarchical levels are prevented from being stored to the server until the edits have been approved for storage in one or more PLs by the at least one of a user or user device with approval authority; and disabling update buttons for the PL which has been edited/annotated on the device screen of the user who entered the edits/annotations until the previously sent edit/annotation updates have been approved or denied by a user and/or user device with approval authority for storage at the remote server.

18. The non-transitory computer readable storage medium of claim 17, wherein the at least one processor device is further configured for generating and associating one or more non-duplicate problem list (PL) categories corresponding to the non-duplicate entries for storage of the non-duplicate entries.

19. The non-transitory computer readable storage medium of claim 17, wherein the problem lists (PLs) are updated in a hierarchical manner such that each PL level prevents automatic uploading to the server upon entry of new data from a lower-level PL until verification by a designated user that higher level PLs includes appropriate access and storage permissions for the new data.

20. The non-transitory computer readable storage medium of claim 17, wherein new medical data entered into a custom problem list (CPL) is stored on a mobile device of the user, and only medical data from the new medical data which is related to categories already present in the hierarchical DPL list stored on the server is uploaded to one or more determined appropriate hierarchical DPLs, and stored in the server.

* * * * *